US010280402B2

(12) United States Patent
Kim et al.

(10) Patent No.: US 10,280,402 B2
(45) Date of Patent: May 7, 2019

(54) IMMUNE-COMPATIBLE CELLS CREATED BY NUCLEASE-MEDIATED EDITING OF GENES ENCODING HLA

(71) Applicants: College of Medicine Pochon CHA University Industry-Academic Cooperation Foundation, Pocheon (KR); INSTITUTE FOR BASIC SCIENCE, Daejeon (KR)

(72) Inventors: Jin Soo Kim, Seoul (KR); Dong Youn Hwang, Seongnam (KR)

(73) Assignees: COLLEGE OF MEDICINE POCHON CHA UNIVERSITY INDUSTRY-ACADEMIC COOPERATION FOUNDATION, Pocheon-si (KR); INSTITUTE FOR BASIC SCIENCE, Daejeon (KR)

( * ) Notice: Subject to any disclaimer, the term of this patent is extended or adjusted under 35 U.S.C. 154(b) by 0 days.

(21) Appl. No.: 15/328,628

(22) PCT Filed: Aug. 6, 2015

(86) PCT No.: PCT/KR2015/008267
§ 371 (c)(1),
(2) Date: Jan. 24, 2017

(87) PCT Pub. No.: WO2016/021972
PCT Pub. Date: Feb. 11, 2016

(65) Prior Publication Data
US 2017/0327795 A1    Nov. 16, 2017

(30) Foreign Application Priority Data

Aug. 6, 2014  (KR) .................... 10-2014-0101203

(51) Int. Cl.
*C12N 5/074* (2010.01)
*C12Q 1/6881* (2018.01)
*C12N 5/0735* (2010.01)
*C07K 14/74* (2006.01)
*C12N 5/073* (2010.01)

(52) U.S. Cl.
CPC ...... *C12N 5/0696* (2013.01); *C07K 14/70539* (2013.01); *C12N 5/0603* (2013.01); *C12N 5/0606* (2013.01); *C12Q 1/6881* (2013.01); *C12N 2501/50* (2013.01); *C12N 2501/70* (2013.01); *C12N 2510/00* (2013.01); *C12Q 2600/156* (2013.01)

(58) Field of Classification Search
None
See application file for complete search history.

(56) References Cited

U.S. PATENT DOCUMENTS

| 6,479,626 | B1 | 11/2002 | Kim |
| 6,903,185 | B2 | 6/2005 | Kim |
| 6,986,887 | B2 | 1/2006 | Lawman |
| 7,153,949 | B2 | 12/2006 | Kim |
| 8,309,312 | B2 | 11/2012 | Lang |
| 2005/0064474 | A1 | 3/2005 | Urnov |
| 2006/0188987 | A1 | 8/2006 | Guschin |
| 2010/0291048 | A1 | 11/2010 | Holmes |
| 2013/0217131 | A1 | 8/2013 | Kim |

FOREIGN PATENT DOCUMENTS

| WO | 2003-100018 | 12/2003 |
| WO | 2007-047894 | 4/2007 |
| WO | 2012/093833 | 7/2012 |
| WO | 2014/065596 | 5/2014 |
| WO | 2014/165177 | 10/2014 |

OTHER PUBLICATIONS

Torikai et al. (Torikai I), "Toward eliminating HLA class I expresion to generate universal cells from allogenic donors" 122(8) Blood 1341-1349 (Jun. 5, 2013).*
Torikai et al. (Torikai II), "ZFN-Driven Gene Editing Prevents HLA-A Expression on Hematopoietic Stem Cells—Improving the Chance of Finding An HLA-Matched Donor" 122 Blood 1655 (2013).*
Mali et al., "RNA-Guided Human Genome Engineering via Cas9" 339 Science 823-826 (Jan. 3, 2013).*
Hiroki Torikai, et al., "HLA and TCR knockout by Zinc Finger Nucleases: toward "off-the-Shelf" Allogeneic T-Cell Therapy for CD19+ Malignancies", 53rd ASH Annual Meeting and Exposition (Blood, Dec. 6, 2010, 116(21), 3766).
Oberg L et al., "Loss or mismatch of MHC class I is sufficient to trigger NK cell-mediated rejection of resting lymphocytes in vivo—role of KARAP/DAP12-dependent and -independent pathways", European Journal of Immunology, Jun. 2004, 34(6): 1646-1653.
Laura Riolobos et al., "HLA engineering of human pluripotent stem cells", Molecular Therapy, Apr. 30, 2013, 21(6): 1232-1241.
Taylor C., et al., "Banking on human embryonic stem cells: estimating the number of donor cell lines needed for HLA matching", (Dec. 10, 2005) Lancet, 366: 2019-2025.
Beerli et al., "Engineering polydactyl zinc-finger transcription factors", (Feb. 2002), Nature Biotechnol., 20:135-141.
Pabo et al., "Design and selection of novel Cys2His2 zinc finger proteins", (Jul. 2001) Ann. Rev. Biochem. 70:313-340.
Isalan et al., "A rapid, generally applicable method to engineer zinc fingers illustrated by targeting the HIV-1 promoter", (Jul. 2001) Nature Biotechnol. 19: 656-660.

(Continued)

*Primary Examiner* — Nancy J Leith
(74) *Attorney, Agent, or Firm* — Lex IP Meister, PLLC

(57) ABSTRACT

The present invention relates to a method for producing immune-compatible cells or a cell population which comprises a step of editing one or two alleles of one or more immune-compatible antigen genes by gene deletion or modification in an isolated cell comprising at least one of the immune-compatible antigen genes selected from HLA (human leukocyte antigen)-A, HLA-B and HLA-DR, to immune-compatible cells produced by the method, and to a cell population comprising the immune-compatible cells produced by the method.

14 Claims, 16 Drawing Sheets

Specification includes a Sequence Listing.

(56) References Cited

OTHER PUBLICATIONS

Segal et al., "Custom DNA-binding proteins come of age: polydactyl zinc-finger proteins", (Dec. 2001) Curr. Opin. Biotechnol. 12:632-637.
Choo et al., "Advances in zinc finger engineering", (Aug. 1, 2000) Curr. Opin. Struct. Biol. 10:411-416.
R. R. Faden et al., "Public Stem Cell Banks: Considerations of Justice in Stem Cell Research and Therapy", Hastings Center Report, N-Hudson, NY, vol. 33, No. 6, Nov. 1, 2003, pp. 13-27.
H. Lin et al., "Multilineage Potential of Homozygous Stem Cells Derived from Metaphase II Oocytes", Stem Cells, Alphamed Press, Dayton, OH, US, vol. 21, No. 2, Jan. 1, 2003, pp. 152-161.
H. Torikai et al., "Toward eliminating Hla class I expression to generate universal cells from allogeneic doners", Blood, 56th Annual Meeting of the American-Society-of-Hematology, vol. 122, No. 8, Aug. 22, 2013, pp. 1341-1349.
L. Ye et al., "Seamless modification of wild-type induced pluripotent stem cells to the natural CCR5 [Delta] 32 mutation confers resistance to HIV infection", Proceedings National Academy of Sciences PNAS, vol. 111, No. 26, Jun. 9, 2014, pp. 9591-9596.
EPO, Extended European Search Report of EP 15830693.6 dated Dec. 22, 2017.
T. Sakuma et al., "Nuclease-mediated genome editing: At the front-line of functional genomics technology", Develop. Growth Differ., Jan. 2014, vol. 56, pp. 2-13.
M. Li et al., "A Cut above the Rest: Targeted Genome Editing Technologies in Human Pluripotent Stem Cells", The Journal of Biological Chemistry, Feb. 2014, vol. 289, No. 8, pp. 4594-4599.
C. -Y. Park et al., "Targeted inversion and reversion of the blood coagulation factor 8 gene in human iPS cells using TALENs", PNAS, Jun. 2014, vol. 111, No. 25, pp. 9253-9258.

* cited by examiner

FIG. 1
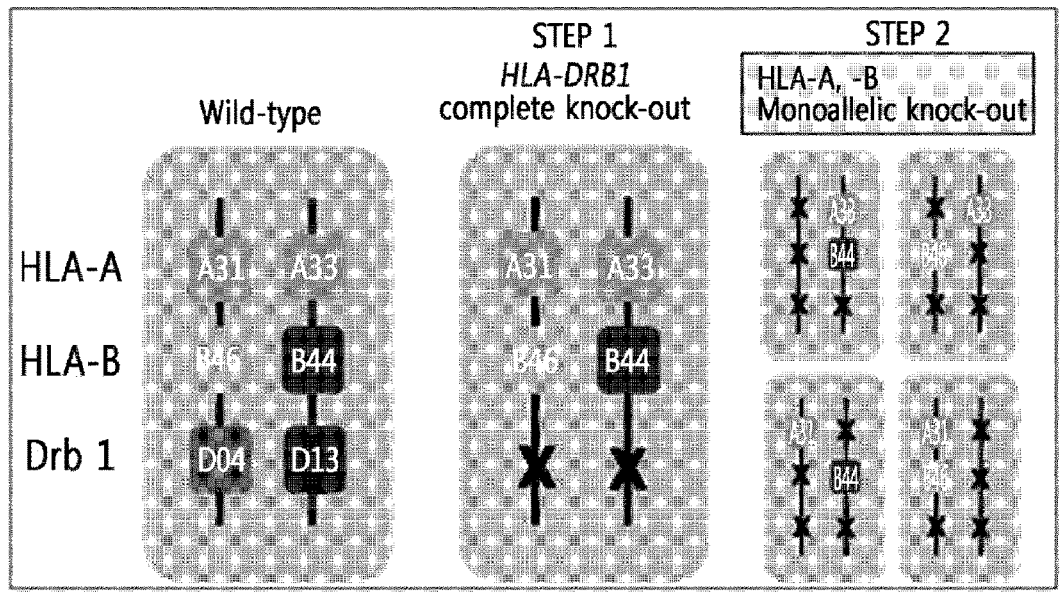
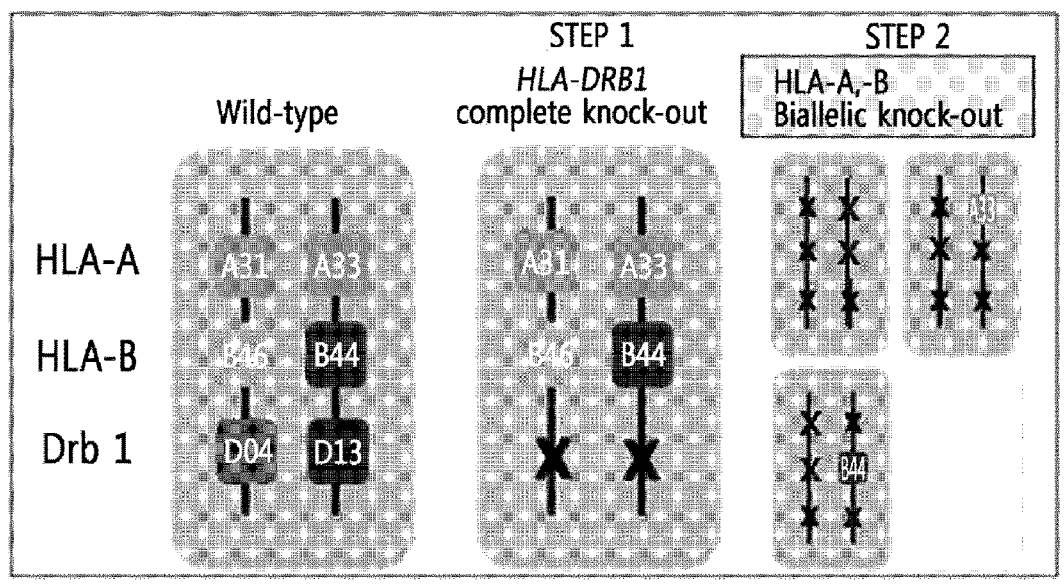

FIG. 9

H9#85
```
WT      GAAGTCAGGTGGTTCCTGAACGGCCAGGAAGAGAAGGCTGGGATGGTGTC         (SEQ ID NO: 16)
DRB1*15 GAAGTCAGGTGGTTCCTGAACGGCC--------------------TGGGATGGTGTC   (-13bp)
DRB1*16 GAAGTCAGGTGGTGGTTCCTGAACGGCCAGGAAG-----GCTGGGATGGTGTC       (-5bp)
```

CHA15#34
```
WT      TCCAGAATGGAGACTGGAGCTTCCA-GACCCCTGGGTGATGCTGGAAACAGTT       (SEQ ID NO: 17)
DRB1*04 TCCAGAATGGAGACTGGAGCTGGACCTTCCAAGACCCCTGGTGATGCTGGAAACAGTT  (+1bp)
DRB1*13 TCCAGAATGGAGACTGGAGACCTTCCAAGACCCCTGGTGATGCTGGAAACAGTT      (+1bp)
``` hiPSC12#13
```
WT      TCCAGAATGGAGACTGGACCTTCCAGACCCTGGTGATGCTGGAAACAGTT          (SEQ ID NO: 15)
DRB1*04 TCCAGAATGGAGAC--------------------------------AGTT          (-32bp)
DRB1*14 TCCAGAATGGAGACTGGACCTTCCAAGACCCTGGTGATGCTGGAAACAGTT         (+1bp)
```

FIG. 15

| | | |
|---|---|---|
| WT | TGGGCAGCTGTGGTGGTGCCCTTCTCTGGAGAAGAGCAGAGAGATACACATGCCATG | (SEQ ID NO: 19) |
| B#53 | TGGGC----------------------------------------------AGCAGAGAGATACACATGCCATG | (-26bp) |

| | | |
|---|---|---|
| WT | TGGGCAGCTGTGGTGGTGCCCTTCTCTGGAGAAGAGCAGAGAGATACACATGCCATG | (SEQ ID NO: 19) |
| B#34 | TGGGCAGCTGTGG----------------------------------CAGAGATACACATGCCATG | (-20bp) |

| | | |
|---|---|---|
| WT | TGGGCAGCTGTGGTGGTGCCCTTCTCTGGAGAAGAGCAGAGAGATACACATGCCATG | (SEQ ID NO: 19) |
| B#98 | TGGGCAGCTGT----------------------------GAAGAGCAGAGAGATACACATGCCATG | (-16bp) |

| | | |
|---|---|---|
| WT | TGGGCAGCTGTGGTGGTGCCCTTCTCTGGAGAAGAGCAGAGAGATACACATGCCATG | (SEQ ID NO: 19) |
| B#134 | TGGGCAGCTGTGGTGGTGCCCTT-----GAAGAGCAGAGAGATACACATGCCATG | (-5bp) |

SEQUENCE LISTING

```
<160> NUMBER OF SEQ ID NOS: 19

<210> SEQ ID NO 1
<211> LENGTH: 23
<212> TYPE: DNA
<213> ORGANISM: Artificial Sequence
<220> FEATURE:
<223> OTHER INFORMATION: HLA-DRB1 target sequence

<400> SEQUENCE: 1
atccaggcag cattgaagtc agg                                            23

<210> SEQ ID NO 2
<211> LENGTH: 23
<212> TYPE: DNA
<213> ORGANISM: Artificial Sequence
<220> FEATURE:
<223> OTHER INFORMATION: HLA-DRB1 target sequence
```

<400> SEQUENCE: 2
ccaggcagca ttgaagtcag gtg                                      23

<210> SEQ ID NO 3
<211> LENGTH: 23
<212> TYPE: DNA
<213> ORGANISM: Artificial Sequence
<220> FEATURE:
<223> OTHER INFORMATION: HLA-DRB1 target sequence

<400> SEQUENCE: 3
ccttccagac cctggtgatg ctg                                      23

<210> SEQ ID NO 4
<211> LENGTH: 23
<212> TYPE: DNA
<213> ORGANISM: Artificial Sequence
<220> FEATURE:
<223> OTHER INFORMATION: HLA-DRB1 target sequence

<400> SEQUENCE: 4
ccagaccctg gtgatgctgg aaa                                      23

<210> SEQ ID NO 5
<211> LENGTH: 23
<212> TYPE: DNA
<213> ORGANISM: Artificial Sequence
<220> FEATURE:
<223> OTHER INFORMATION: HLA-A target sequence

<400> SEQUENCE: 5
ccctgcggag atcacactga cct                                      23

<210> SEQ ID NO 6
<211> LENGTH: 23
<212> TYPE: DNA
<213> ORGANISM: Artificial Sequence
<220> FEATURE:
<223> OTHER INFORMATION: HLA-A target sequence

<400> SEQUENCE: 6
cctgcggaga tcacactgac ctg                                      23

<210> SEQ ID NO 7
<211> LENGTH: 23
<212> TYPE: DNA
<213> ORGANISM: Artificial Sequence
<220> FEATURE:
<223> OTHER INFORMATION: HLA-A target sequence

<400> SEQUENCE: 7
gagaccaggc ctgcagggga tgg                                      23

<210> SEQ ID NO 8
<211> LENGTH: 23
<212> TYPE: DNA
<213> ORGANISM: Artificial Sequence
<220> FEATURE:
<223> OTHER INFORMATION: HLA-A target sequence

<400> SEQUENCE: 8
cacctgccat gtgcagcatg agg                                      23

<210> SEQ ID NO 9

```
<211> LENGTH: 23
<212> TYPE: DNA
<213> ORGANISM: Artificial Sequence
<220> FEATURE:
<223> OTHER INFORMATION: HLA-B target sequence

<400> SEQUENCE: 9
accctgaggt gctgggccct ggg                                              23

<210> SEQ ID NO 10
<211> LENGTH: 23
<212> TYPE: DNA
<213> ORGANISM: Artificial Sequence
<220> FEATURE:
<223> OTHER INFORMATION: HLA-B target sequence

<400> SEQUENCE: 10
gatcacactg acctggcagc ggg                                              23

<210> SEQ ID NO 11
<211> LENGTH: 23
<212> TYPE: DNA
<213> ORGANISM: Artificial Sequence
<220> FEATURE:
<223> OTHER INFORMATION: HLA-B target sequence

<400> SEQUENCE: 11
acactgacct ggcagcggga tgg                                              23

<210> SEQ ID NO 12
<211> LENGTH: 23
<212> TYPE: DNA
<213> ORGANISM: Artificial Sequence
<220> FEATURE:
<223> OTHER INFORMATION: HLA-B target sequence

<400> SEQUENCE: 12
gacctggcag cgggatggcg agg                                              23

<210> SEQ ID NO 13
<211> LENGTH: 23
<212> TYPE: DNA
<213> ORGANISM: Artificial Sequence
<220> FEATURE:
<223> OTHER INFORMATION: HLA-B target sequence

<400> SEQUENCE: 13
ccttctggag aagagcagag ata                                              23

<210> SEQ ID NO 14
<211> LENGTH: 55
<212> TYPE: DNA
<213> ORGANISM: Artificial Sequence
<220> FEATURE:
<223> OTHER INFORMATION: HLA-DRB1  target sequence

<400> SEQUENCE: 14
agaatggaga ttggaccttc cagaccctgg tgatgctgga aacagttcct cggag           55

<210> SEQ ID NO 15
<211> LENGTH: 56
<212> TYPE: DNA
<213> ORGANISM: Artificial Sequence
<220> FEATURE:
<223> OTHER INFORMATION: HLA-DRB1  target sequence

<400> SEQUENCE: 15
```

```
tccagaatgg agactggacc ttccagaccc tggtgatgct ggaaacagtt cctcg g        56

<210> SEQ ID NO 16
<211> LENGTH: 50
<212> TYPE: DNA
<213> ORGANISM: Artificial Sequence
<220> FEATURE:
<223> OTHER INFORMATION: HLA-DRB1 target sequence

<400> SEQUENCE: 16
gaagtcaggt ggttcctgaa cggccaggaa gagaaggctg ggatggtgtc                50

<210> SEQ ID NO 17
<211> LENGTH: 50
<212> TYPE: DNA
<213> ORGANISM: Artificial Sequence
<220> FEATURE:
<223> OTHER INFORMATION: HLA-DRB1 target sequence

<400> SEQUENCE: 17
tccagaatgg agactggacc ttccagaccc tggtgatgct ggaaacagtt                50

<210> SEQ ID NO 18
<211> LENGTH: 51
<212> TYPE: DNA
<213> ORGANISM: Artificial Sequence
<220> FEATURE:
<223> OTHER INFORMATION: HLA-A target sequence

<400> SEQUENCE: 18
ggagcagaga tacacctgcc atgtgcagca tgagggtctc cccaagcccc t              51

<210> SEQ ID NO 19
<211> LENGTH: 52
<212> TYPE: DNA
<213> ORGANISM: Artificial Sequence
<220> FEATURE:
<223> OTHER INFORMATION: HLA-B target sequence

<400> SEQUENCE: 19
tgggcagctg tggtggtgcc ttctggagaa gagcagagat acacatgcca tg             52
```

IMMUNE-COMPATIBLE CELLS CREATED BY NUCLEASE-MEDIATED EDITING OF GENES ENCODING HLA

TECHNICAL FIELD

The present invention relates to a method for producing immune-compatible cells or cell populations, comprising editing one or two alleles of one or more immune-compatible antigen genes by gene deletion or modification in an isolated cell, comprising at least one of the immune-compatible antigen genes selected from human leukocyte antigen (HLA)-A, HLA-B and HLA-DR, to immune-compatible cells produced by the above production method, and to a cell population comprising the immune-compatible cells produced by the above production method.

BACKGROUND ART

Human embryonic stem cells (hESCs) are pluripotent cells capable of unlimited self-renewal and can differentiate into the cell types of all three germ layers. The first use of hESCs heralded a new era in regenerative medicine because under appropriate conditions hESCs respond to external signals and can be coaxed to differentiate into specialized cell types such as functional cardiomyocytes and pancreatic β cells. These characteristics make them a valuable cell resource in regenerative medicine. Patients suffering from neurodegenerative, autoimmune, cardiovascular and hematopoietic diseases are potential beneficiaries of stem cell therapy. Despite their tremendous potential, immune rejection of allogeneic hESC-derived cells is a major obstacle to the use of the cells in clinic. Cell surface expression of human leukocyte antigens (HLA), which are encoded by genes in the major histocompatibility complex are the major immunologic barrier.

Unique properties of hESCs can be reestablished in somatic cells by somatic nuclear transfer (SNT) or forced expression of 4 transcription factors Oct4 (O), Sox2 (S), Klf4 (K), and c-Myc (M), which can induce somatic cells into ESC-like cells, which are named induced pluripotent stem cells (iPSCs). These two approaches allow derivation of patient specific pluripotent stem cells. Importantly, since these cells are made from a patient's own cells, it is considered that their immune system will not reject them.

However, since SNT mediated reprogramming of human somatic cells is in its infancy, has low efficiency and requires oocyte donation, it cannot yet offer a practical solution. While relatively simple derivation of iPSCs seems promising, according to recent reports, transcription factor-based reprogramming is associated with incomplete epigenetic reprogramming. Therefore using these cells in clinic requires detailed examination of iPSC clones, which is cumbersome. Moreover, generating pluripotent stem cells under good manufacturing practices (GMP) for individual patients is likely to be financially prohibitive.

One approach to overcoming the immunological barrier to stem-cell transplantation is to establish clinical-grade hESC/iPSC/SNT-hESC banks with HLA haplotypes, which will match a significant proportion of the population. However derivation of hESC/iPSC/SNT-hESC lines under current good manufacturing practice (cGMP) requires investments of substantial amounts of money and time.

Another solution to avoid immune rejection of hESC derivatives is genetic manipulation of HLA molecules. By using zinc finger nucleases, Torikai and colleagues selectively eliminated human leukocyte antigen (HLA) class I in ESCs and demonstrated that HLA-A cells could escape lysis from HLA-restricted cytotoxic T lymphocytes. However HLA class I complete knock-out cells are targets for NK-cell-mediated cytotoxicity (Oberg L etc., Eur J Immunol., 2004, 34(6): 1646-1653).

In another study, Riolobos and colleagues disrupted beta-2 microglobulin (B2M) which encodes the accessory chain of major histocompatibility complex (MHC) class I molecules and is required for their surface expression (Laura Riolobos etc., 2013, 21(6): 1232-1241). Therefore, the homozygous deletion of the B2M gene prevents the surface translocation of class I HLA molecules and reduces immunogenicity. However this approach offers a limited solution because it has been reported that hematopoietic stem cells lacking the B2M gene are eliminated by NK cells. Although enforced expression of less polymorphic HLA-E or HLA-G-B2M chimeric proteins protects class I negative cells from NK-cell-mediated lysis in vitro, any in vivo data has not been reported yet.

More recently, cytotoxic T lymphocyte-associated protein 4 (CTLA4)-immunoglobulin and programmed cell death ligand 1 (PDL1) knock-in human ESCs (hESCs) were shown to simultaneously disrupt T cell costimulatory pathways and activate T cell inhibitory pathways in humanized mice. It is well known that infected cells are also subject to immune response. There is no in vivo study showing if these CTLA4 and PDL1 double knock-in cells can be eliminated by immune cells when they become infected.

It appears the monoallelic mutation of HLA molecules and consequent derivation of HLA homozygous hESCs might offer a solution for overcoming immune rejection of hESCs. Creation of a small library of homozygous hESCs from existing hESC lines could cover significant percentage of the human population.

DISCLOSURE

Technical Problem

The present inventors have conducted intensive research to develop cells for transplantation carrying an HLA gene in a hemizygous type, thereby not causing immunorejection in a recipient, and a process for constructing cell populations comprising the same. As a result, the inventors have discovered that cells for transplantation which are immune-compatible for many recipients, and cell populations comprising the same, can be produced by editing HLA-1, HLA-B and HLA-DR genes, that is, three major HLA type determinant genes, thus completing the present invention.

Technical Solution

One objective of the present invention is to provide a method for producing immune-compatible cells or cell populations, comprising editing one or two alleles of one or more immune-compatible antigen genes by gene deletion or modification in an isolated cell, comprising at least one of the immune-compatible antigen genes selected from human leukocyte antigen (HLA)-A, HLA-B and HLA-DR.

Another objective of the present invention is to provide a method for producing immune-compatible cells or cell populations, comprising editing one or two alleles of one or more immune-compatible antigen genes by gene deletion or modification in an isolated cell, wherein at least one of the immune-compatible antigen genes selected from human leukocyte antigen (HLA)-A, HLA-B and HLA-DR has a heterozygous genotype.

Another objective of the present invention is to provide immune-compatible cells produced by the above production method.

Another objective of the present invention is to provide a cell population comprising the immune-compatible cells produced by the above production method.

Another objective of the present invention is to provide a method for producing immune-compatible cells or a cell population comprising: (a) editing one or two alleles of one or more immune-compatible antigen genes by gene deletion or modification in an isolated cell, wherein at least one of the immune-compatible antigen genes selected from human leukocyte antigen (HLA)-A, HLA-B and HLA-DR has a heterozygous genotype, and (b) collecting the cells produced in step (a).

Advantageous Effects

According to the present invention, cells which are immune-compatible to many recipients can be produced by editing critical histocompatibility antigen (HLA) genes which may cause immunorejection from allogeneic cells for transplantation. Accordingly, when several kinds of different cells are constructed by using this process and subjected to banking, it is possible to provide a very important basis for cell therapy which can be used for allogeneic transplantation immediately when needed.

BRIEF DESCRIPTION OF THE DRAWINGS

FIG. 1 is a schematic view illustrating a method for producing immune-compatible cells and constructing a cell population by knocking out one or both parental and maternal alleles of HLA-A and HLA-B genes and knocking out both of two alleles of HLA-DRB1 genes.

FIG. 9 shows the results of identifying whether or not, after Cas9 proteins and DRB1 guide RNA are introduced into human embryonic stem cells H9 #85 and CHA15 #34, and human induced pluripotent stem cells hiPSC12 #13 via electroporation, the indel is induced in the site of the target sequences in the DRB1 gene through a sequence analysis.

FIG. 15 shows the results of analyzing HLA-B sequences of #53, #34, #98, and #134 clones.

BEST MODE

Figure 2:
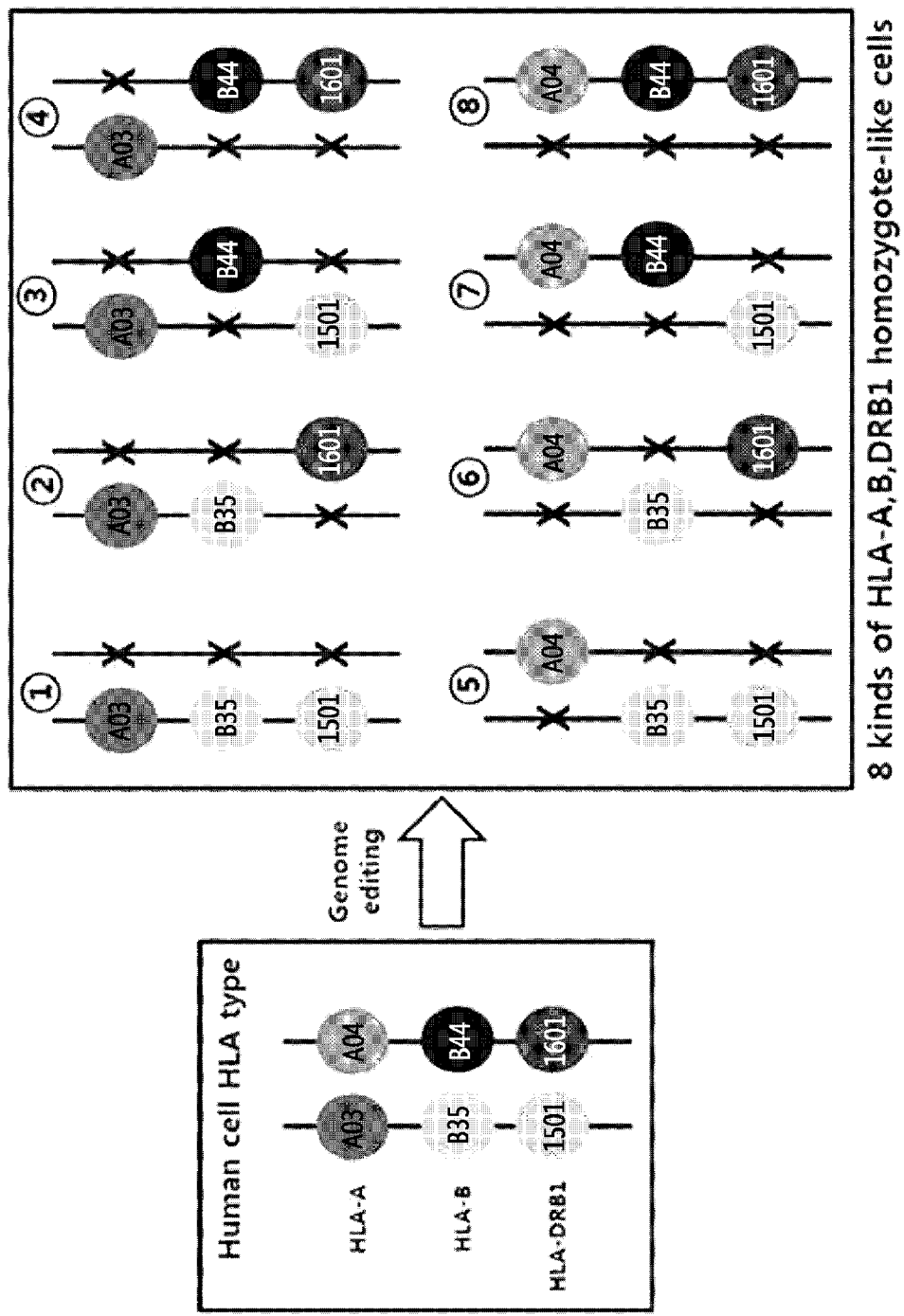
FIG. 2 is an exemplary view indicating that, when knocking out one of parental and maternal alleles of HLA-A, HLA-B, and HLA-DRB1 genes, a total of eight kinds of homozygous-like cells relative to HLA-A, HLA-B, and HLA-DRB1 genes can be produced from the cells of one donor.

In one embodiment, the present invention provides a method for producing immune-compatible cells, comprising editing one or two allele of one or more immune-compatible antigen genes by gene deletion or modification in an isolated cell, comprising at least one of the immune-compatible antigen genes selected from human leukocyte antigen (HLA)-A, HLA-B and HLA-DR. The isolated cell may comprise the immune-compatible antigen genes which are heterozygous or homozygous, and the editing step may be editing two alleles.

Another embodiment, the present invention provides a method for producing immune-compatible cells, comprising editing one or two allele of oen or more immune-compatible antigen genes by gene deletion or modification in an isolated cell, wherein at least one of the immune-compatible antigen genes selected from human leukocyte antigen (HLA)-A, HLA-B and HLA-DR has a heterozygous genotype. Also, the above production method may be a method for producing a cell population including the immune-compatible cells.

In addition, the above production method may be a method for producing immune-compatible cells, comprising editing one or two allele of the immune-compatible antigen gene by gene deletion or modification in an isolated cell, wherein an immune-compatible antigen gene, HLA-A or HLA-B, has a heterozygous genotype. As described above, the production method can be a process for producing a cell population including the immune-compatible cells. However, these are not particularly limited thereto.

The most significant barrier that all cell therapy must overcome in order to be used for therapeutic purposes is immunorejection. The entities that cause the immunorejection are 6 types of HLA (HLA-A, HLA-B, HLA-C, HLA-DP, HLA-DQ, and HLA-DR) cell surface proteins called the major histocompatibility antigen (MHC). A human is known to express six species derived from paternal genes and six species derived from maternal genes, that is, a total of six pairs. More specifically, general somatic cells express a total of only three pairs, i.e., HLA-A, HLA-B and HLA-C belonging to MHC class I, and the immune cells express a total of 6 pairs, a sum of MHC class I and MHC class II.

The role of HLA surface antigens is to display fragments of the proteins present in the cells on the cell surface and to enable infections or mutations that might occur in the body to be detected by the immune cells. For this reason, they are also called antigen presenting proteins.

When conducting cell therapy or tissue transplantation, including bone marrow transplantation, if these antigen presenting proteins are not autologous, they become the major targets of the immune cells present in the body of a transplant recipient. This is because each person has a number of genetic polymorphisms on the respective HLA genes. For example, because HLA-A genes of the donor and HLA-A genes of the recipient are not the same, the immune cells in the body of the recipient recognize the difference and attack the donor cells. Ultimately, this leads to the failure of transplantation due to immunorejection. This phenomenon is applicable to all of HLA-A genes as well as HLA-B, HLA-C, HLA-DP, HLA-DQ and HLA-DR genes. Due to the clinical experience accumulated so far, it has been known that it is possible to ensure a considerable success rate of transplantation even by matching three pairs of HLA-A, HLA-B and HLA-DRB1 with many of polymorphisms (or, four pairs including up to HLA-C), without matching all six pairs of HLA genes (MHC class I and class II).

In this regard, the present invention is characterized in that it provides a method capable of producing immune-compatible cells, wherein immune-compatible antigens have homozygous-like or hemizygous genotypes by gene deletion or modification.

In the present invention, the term "homozygosis of immune-compatible antigens" means that one, two or three genotypes selected from the HLA-A, HLA-B, and HLA-DR genes paternally and maternally inherited from the donor have exactly the same HLA genotypes. Specifically, the homozygosis of immune-compatible antigens may include that the genotypes of the respective HLA-A and HLA-B genes are completely the same, but is not limited thereto. In addition, when containing the HLA-DR gene, the homozygosis of immune-compatible antigens may include the genotypes of the respective HLA-A, HLA-B, and HLA-DR genes being completely the same, but is not intended to be limited thereto.

For a more specific non-limiting example, the cells derived from the donor (paternal and maternal HLA genotypes are the same) having [HLA-A*11 (hereinafter, HLA omitted), B*51, DRB1*16 (paternal)/A*11, B*51, DRB1*16 (maternal)] may be homozygous with the immune-compatible antigens. In this case, the transplantation is available to recipients of all the combinations of HLA genotypes in which only three among six pairs are identical, such as the recipient of [A*11, B*51, DRB1*16 (paternal)/A*24, B*34, DRB1*08 (maternal)], the recipient of [A*11, B*15, DRB1*04 (paternal)/A*24, B*51, DRB1*16 (maternal)], the recipient of [A*03, B*08, DRB1*16 (paternal)/A*11, B*51, DRB1*09 (maternal)], or the recipient of [A*02, B*51, DRB1*07 (paternal)/A*11, B*44, DRB1*16 (maternal)]. There is a report that, for the immune-compatible cell therapy for more than 90% of people, about 200 species of cell lines carrying the immune-compatible homozygous antigens are necessary [Taylor C, Banking on human embryonic stem cells: estimating the number of donor cell lines needed for HLA matching, 2005, Lancet, 366: 2019-2025]. Therefore, when finding 200 donors having homozygosis of immune-compatible antigens different from each other through the HLA genotype screening, it is possible to secure in advance the immune-compatible cell lines capable of being transplanted to more than 90%, but there is a great difficulty in conducting the HLA gene screening for so many persons.

In one aspect for solving the above-mentioned problems, the present inventors have developed a method for producing homozygous-like cells using a method called gene editing, genome editing or genome engineering.

In the present invention, the term "homozygous-like" refers to having only one allele by knocking out or knocking in one allele in one pair of particular heterozygous alleles. For the purposes of the present invention, homozygous-like refers to a state in which one, two, or three genes selected from the group consisting of HLA-A, HLA-B and HLA-DR have only one allele. More specifically, in the present invention, homozygous-like may be a state in which HLA-A, HLA-B, and optionally, HLA-DR genes have only one allele, but is not limited thereto.

In the present invention, the "immune-compatible cell" may be a cell in which the immune-compatible antigens, specifically one, two, or three alleles selected from the group consisting of HLA-A, HLA-B and HLA-DR genes are present as homozygous-like, but are not particularly limited thereto. More specifically, it may be a cell in which HLA-A, HLA-B, and optionally, HLA-DR genes may be present as homozygous-like.

Furthermore, the HLA-DR gene in the immune-compatible cell may be that in which both alleles are completely removed (knocked out), but is not limited thereto. In this case, the immune-compatible cell can be produced by deleting or modifying one allele of each of HLA-A or HLA-B gene by the gene editing in a cell in which one pair of alleles of the HLA-DR gene is knocked out or in an isolated cell, wherein one or both of HLA-A or HLA-B gene is heterozygous. Alternatively, in the isolated cell, wherein one or both of HLA-A or HLA-B gene is heterozygous, one allele of each of HLA-A or HLA-B gene is deleted or modified by the gene editing, followed by deleting one pair of HLA-DR genes. In addition, in the present invention, one or more genes selected from HLA-A, HLA-B, and HLA-DR in the immune-compatible cell may be that in which both alleles are completely removed (knocked out). However, the present invention is not intended to be limited by the above-described examples.

Through this, it is possible to obtain a cell that can be transplanted to recipients with a combination of only two or only one identical HLA genotypes among the six pairs.

Figure 3:
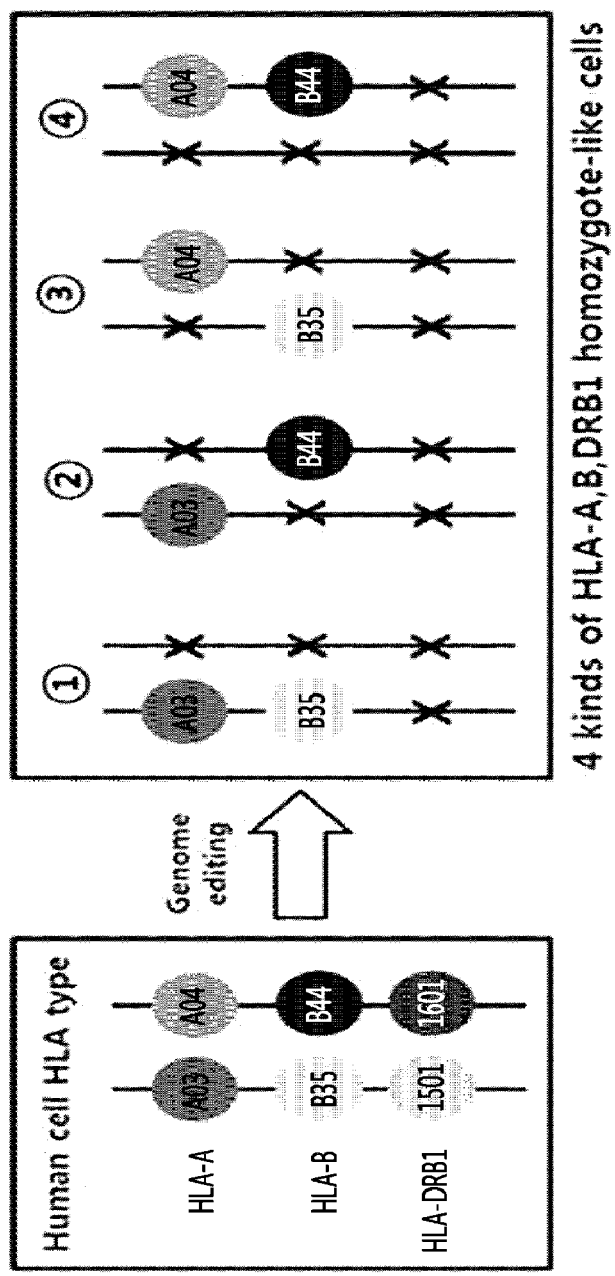
FIG. 3 is an exemplary view indicating that, when knocking out one of the parental and maternal alleles of HLA-A, and HLA-B genes and knocking out both of said two alleles of HLA-DRB1 gene, a total of four kinds of homozygous-like cells relative to HLA-A, HLA-B, and HLA-DRB1 genes can be produced from the cells of one donor.

Further, according to the process of the present invention, when one (paternal or maternal) allele of the major histocompatibility antigen genes is deleted or modified by the gene editing, it is possible to obtain genetically homozygous-like cells as described above. Therefore, when the thus obtained cells, in which the respective alleles are knocked out or knocked in one-by-one, are collected, finally several types of cells which exhibit homozygous effects can be obtained from the cells of one donor (see FIGS. 1 to 3). Thus, it can provide a great advantage of obtaining more than 200 immune-compatible cells capable of being transplanted into more than 90% of people.

In one specific embodiment of the present invention, the immune-compatible cells can be those in which one or two allele of heterozygous genes is edited by gene deletion or modification. In particular, the deletion may be made by knock-out and the modification may be made by knock-in, but is not limited thereto.

The techniques of genome editing/gene editing are those capable of introducing a target-directed mutation into the genomic sequence of animal and plant cells including human cells, and can knock-out or knock-in a certain gene or introduce a mutation even in non-coding DNA sequences that do not produce a protein. The method of the present invention can produce the immune-compatible cells through the technologies of genome editing or gene editing.

In one specific embodiment of the present invention, the gene editing technology is characterized by using a target-specific nuclease.

In the present invention, the term "target-specific nuclease" may refer to a nuclease capable of recognizing and cleaving a specific position of DNA on the genome of interest. The nuclease may include a nuclease in which a domain recognizing a specific target sequence on the genome and a domain cleaving the same have been fused. Examples thereof may include, but are not limited to, a meganuclease, or an engineered nuclease, especially a transcription activator-like effector nuclease (TALEN) in which a transcription activator-like (TAL) effector derived from a plant pathogenic gene that is a domain recognizing a specific target sequence on the genome and a cleavage domain have been fused, a zinc-finger nuclease, or a RGEN (RNA-guided engineered nuclease) derived from the CRISPR microbial immune system. The method using the RGEN for the purposes of the present invention is simple and can achieve more desirable results, but is not intended to be particularly limited thereto. Further, for the purposes of this invention, the aforementioned gene editing can be performed by using HLA-A specific nucleases, HLA-B specific nucleases or HLA-DR-specific nucleases, and the nuclease is preferably an engineered nuclease, but is not limited thereto.

When performing the knock-out or knock-in process using the nuclease, specifically the engineered nuclease, unlike the knock-out process which does not necessarily use a donor DNA except for the nuclease, the knock-in process uses a donor DNA together with the nuclease. The donor DNA refers to DNA including a gene to be introduced at a position on the chromosome cleaved by the nuclease. The donor DNA may include a left flanking arm and a right flanking arm for recombination. Further, the donor DNA may optionally include a selection marker, but is not limited thereto.

The target-specific nuclease recognizes a specific nucleotide sequence in the genome of animal and plant cells, including human cells to thereby cause a double strand break (DSB). The DSB is effectively repaired by homologous recombination or a non-homologous end-joining (NHEJ) mechanism within the cells. During this process, a desired mutation can be introduced into a target location. The target-specific nuclease may be artificial or engineered and non-naturally occurring.

The nuclease may be a zinc-finger nuclease (ZFN).

The ZFN includes a selected gene, and a zinc-finger protein engineered to bind to a target site in a cleavage domain or a cleavage half-domain. The ZFN may be an artificial restriction enzyme including a zinc-finger DNA binding domain and a DNA cleavage domain. Here, the zinc-finger DNA binding domain can be one that is engineered to bind to a selected sequence. For example, Beerli et al. (2002) Nature Biotechnol. 20:135-141; Pabo et al. (2001) Ann. Rev. Biochem. 70:313-340; Isalan et al, (2001) Nature Biotechnol. 19: 656-660; Segal et al. (2001) Curr. Opin. Biotechnol. 12:632-637; and Choo et al. (2000) Curr. Opin. Struct. Biol. 10:411-416 may be incorporated herein by reference compared with a naturally occurring zinc-finger protein, an engineered zinc-finger binding domain can have a novel binding specificity. The engineering method includes the rational design and the selection of various types, but is not limited thereto. The rational design includes the use of a database comprising, for example, a triple (or quadruple) nucleotide sequence, and individual zinc finger amino acid sequences. At this time, the respective triple or quadruple nucleotide sequences are combined with one or more sequences of zinc fingers which bind to a certain triple or quadruple sequence.

Selection of a target sequence, the design and construction of fusion proteins (and polynucleotides encoding them) are known to those skilled in the art, and are described in detail in U.S. Patent Publication Nos. 2005/0064474 and 2006/0188987, the entire contents of which are incorporated herein by reference. Moreover, as disclosed in these references and the other references in the relevant art, zinc finger domains and/or multiple-zinc finger proteins can be linked together by any suitable linker sequences, for example, a linker including five or more amino acids in length. Examples of the linker sequence of six or more amino acids in length are disclosed in U.S. Pat. Nos. 6,479,626; 6,903,185; and 7,153,949. The proteins described herein can comprise any combination of suitable linkers between each of the zinc fingers of the proteins.

In addition, the nuclease such as ZFN includes nuclease active portions (i.e., cleavage domain and cleavage half-domain). As has been known, for example, as in the cleavage domain of the nuclease different from the zinc finger DNA binding domain, the cleavage domain may be heterologous to the DNA binding domain. The heterologous cleavage domain can be derived from any endonuclease or exonuclease. An exemplary endonuclease from which the cleavage domain can be derived may include a restriction endonuclease and a meganuclease, but is not limited thereto.

Similarly, the cleavage half-domain may be derived from any nuclease or portion thereof that requires dimerization for cleavage activity as set forth above. When a fusion protein includes a cleavage half-domain, typically two fusion proteins are required for cleavage. Alternatively, a single protein including two cleavage half-domains can be used. The two cleavage half-domains may also be derived from the same endonuclease (or functional fragments thereof), or each cleavage half-domain may be derived from different endonucleases (or functional fragments thereof). Further, it is preferable to arrange the target sites of the two fusion proteins such that the half-cleavage domains are spatially oriented with respect to each other by binding the two fusion proteins to the target sites thereof, and thereby, the cleavage half-domain forms functional cleavage domains, for example, by dimerization. Therefore, in one embodiment, the neighboring edge of the target site is separated by 5 to 8 nucleotides or 15 to 18 nucleotides. However, any integer number of nucleotides or nucleotide pairs may be interposed between the two target sites (e.g., 2 to 50 nucleotide pairs or more). In general, the cleavage site is placed between the target sites.

The restriction endonucleases (restriction enzymes) are present in many species, and they can be sequence-specifically bound to DNA (at a target site), thus cleaving DNA at or near the binding site. Some restriction enzymes (e.g., Type IIS) cleave DNA at a site removed from the recognition site, and include separable binding and cleavable domains. For example, Type IIS enzyme FokI catalyzes a double-stranded cleavage of DNA in nine nucleotides from the recognition site on one strand and in 13 nucleotides from the recognition site on the remaining one strand. Thus, in one embodiment, the fusion protein includes at least one cleavage domain (or cleavage half-domain) from Type IIS restriction enzyme and one or more zinc-finger domains (that may or may not be engineered).

In the present invention, the term "TALEN" refers to a nuclease that can recognize and cleave the target region of DNA. TALEN refers to a fusion protein comprising a TALE domain and a nucleotide cleavage domain. In the present invention, the term "TAL effector nuclease" and "TALEN" can be interchangeably used. The TAL effector has been known as a protein secreted through their Type III secretion system when various plant species are infected with *Xanthomonas* bacteria. The protein can be associated with a promoter sequence in the host plant to thereby activate the expression of a plant gene that helps bacterial infections. The protein recognizes a plant DNA sequence via a central repeat domain composed of 34 or less various numbers of amino acids repeats. Therefore, it is believed that TALE may be a novel platform used as a tool in the genome engineering. However, in order to produce a functional TALEN having a genome-editing activity, a few key parameters previously unknown up to now must be defined as follows: i) a minimum DNA-binding domain of TALE, ii) a length of the spacer between two half-sites forming one target region, and iii) a linker or a fusion junction linking the FokI nuclease domain to dTALE.

In the present invention, the TALE domain refers to a protein domain that binds to a nucleotide through one or more TALE-repeating modules in a sequence-specific manner. The TALE domain includes at least one TALE-repeating module, more particularly 1 to 30 TALE-repeating modules, but is not limited thereto. In the present invention, the term "TAL effector domain" and "TALE domain" are interchangeably used. The TALE domain may comprise half of the TALE-repeating module. In connection with the TALEN, the entire contents disclosed in International Patent Publication WO/2012/093833 or U.S. Patent Publication No. 2013-0217131 are incorporated herein by reference.

In the present invention, the term "RGEN" refers to a nuclease that contains a target DNA specific guide RNA and a Cas protein as a component. That is, for example, the RGEN in the present invention may comprise a guide RNA that specifically bind to a particular sequence of the HLA-A, HLA-B, or HLA-DR gene, and a Cas protein, but is not limited thereto.

In the present invention, the RGEN can be applied to cells in the form of a target DNA specific guide RNA or a DNA encoding the guide RNA; and a separated Cas protein or a nucleic acid encoding the Cas protein, but is not limited thereto.

In a more specific embodiment of the present invention, the RGEN can be applied to cells in the form of 1) a target DNA specific guide RNA and a separated Cas protein, and 2) a DNA encoding the guide RNA and a nucleic acid encoding the Cas protein.

Transferring the RGEN to the cells in the form of the above 1) is referred to as "RNP delivery", but is not limited thereto.

When applied in the form of the isolated guide RNA, the guide RNA may be transcribed in vitro, but is not limited thereto.

In addition, the DNA encoding the guide RNA and the nucleic acid encoding the Cas protein may be used as an isolated nucleic acid itself, and can be present in the form of a vector containing an expression cassette for expressing the guide RNA and/or Cas protein, but is not limited thereto.

The vector may be a viral vector, a plasmid vector or an *Agrobacterium* vector, and the type of the viral vector may include AAV (Adeno-associated virus), but is not limited thereto.

The DNA encoding the guide RNA and the nucleic acid encoding the Cas protein are present in individual vectors, respectively, or can be present in the same vector, but are not limited thereto.

Each of the embodiments described above may be completely applied even with respect to more specific embodiments described in the present specification.

In the present invention, the RGEN may include a guide RNA specifically binding to a specific sequence of the HLA-A, HLA-B or HLA-DR gene or a DNA encoding the same, and a Cas protein or a nucleic acid sequence encoding the same, but is not limited thereto. In the present invention, the term "Cas protein" is a major protein component of the CRISPR/Cas system and is a protein capable of forming an activated endonuclease or nickase.

The Cas protein can form a complex with crRNA (CRISPR RNA) and tracrRNA (trans-activating crRNA) to thereby exhibit its activity.

The Cas protein or genetic information thereon may be obtained from known databases such as GenBank of NCBI (National Center for Biotechnology Information). More specifically, the Cas protein may be a Cas9 protein. Moreover, the Cas protein may be a *Streptococcus* genus-derived protein, particularly a *Streptococcus pyogenes*-derived Cas protein, and more particularly a Cas9 protein. In addition, the Cas protein may be a *Campylobacter* genus-derived protein, particularly a *Campylobacter jejuni*-derived Cas protein, and more particularly a Cas9 protein. However, the present invention is not intended to be limited to the above-mentioned examples.

Further, the Cas protein used in the present invention includes, in addition to the naturally occurring proteins, an endonuclease activated in cooperation with the guide RNA, or a variant thereof capable acting as a nickase. The variant of the Cas9 protein may be a mutein of Cas9 in which a catalytic aspartate residue has been changed to any other amino acid. Specifically, the other amino acid may be alanine, but is not limited thereto.

In the present invention, the Cas protein may be a recombinant protein.

When used in the context of cells, nucleic acids, proteins or vectors, the term "recombinant" refers to, for example, modified cells, nucleic acids, proteins or vectors in which a heterologous nucleic acid or a protein is introduced, a native nucleic acid or a protein is modified, or cells are derived from the modified cells. Thus, for example, the recombinant Cas protein may be produced by reconstructing the amino acid sequence encoding the Cas protein using the human codon table.

The Cas protein or nucleic acid encoding the same can be in a form in which the Cas protein allows action in the nucleus.

The separated Cas protein can also be a form that is easy to introduce into the cell. As an example, the Cas protein may be linked to a cell penetrating peptide or a protein transduction domain. The protein transduction domain can be a poly-arginine or HIV-derived TAT protein, but is not limited thereto. It is well known in the art that there are various types of the cell-penetrating peptide or protein transduction domain, in addition to the above stated examples, and so a person skilled in the art can apply various examples to the present invention without being limited to the above.

In addition, the nucleic acid encoding the Cas proteins may further comprise a nuclear localization signal (NLS) sequence. Thus, an expression cassette comprising a nucleic acid encoding the Cas protein may comprise the NLS sequence as well as a regulatory sequence such as a promoter sequence for expressing the Cas protein. However, the invention is not limited thereto.

The Cas protein may be linked to a tag facilitating separation and/or purification. As an example, a small peptide tag such as a His tag, a Flag tag or an S-tag, or a GST (glutathione S-transferase) tag, an MBP (maltose binding protein) tag and the like can be linked according to the purpose, but are not limited thereto.

In the present invention, the term "guide RNA" refers to a target DNA-specific RNA which specifically bind to a particular target sequence, and it binds to the Cas protein so that the Cas protein can be directed to the target DNA.

In the present invention, the guide RNA may be a dual RNA including two RNAs, that is, crRNA (CRISPR RNA) and tracrRNA (trans-activating crRNA) as a component; or a form comprising a first region including a sequence that can make base pair with complementary sequence to the target DNA sequence and a second region including a sequence interacting with the Cas protein, more particularly sgRNA (single-chain RNA) in which the main parts of crRNA and tracrRNA have been fused.

The sgRNA may include a portion having a sequence that can make base pair with complementary sequence to the target DNA sequence (this may be also referred to as a spacer region, a target DNA recognition sequence, a base pairing region, etc.) and a hairpin structure for Cas protein binding. More particularly, the sgRNA may include a portion having a sequence that can make base pair with complementary sequence to the target DNA sequence, a hairpin structure for Cas protein binding and a terminator sequence. The above-described structure may be present sequentially in the order of 5' to 3'. However, it is not limited thereto.

If the guide RNA comprises the essential portion of crRNA and tracrRNA and a portion that can make base pair with complementary to a target, any guide RNA may be used in the present invention.

The crRNA may hybridize with a target DNA.

The RGEN is composed of a Cas protein and a dual RNA, or can be composed of a Cas protein and sgRNA. Further, the RGEN may include, as a component, a nucleic acid encoding the Cas protein and a nucleic acid encoding the dual RNA; or include a nucleic acid encoding the Cas protein and a nucleic acid encoding the sgRNA, but is not limited thereto.

The guide RNA, particularly crRNA or sgRNA, may include a sequence that can make base pair with complementary sequence to the target DNA sequence, and further include one or more additional nucleotides at an upstream portion of crRNA or sgRNA, particularly at the 5' end of crRNA of sgRNA or dual RNA. The additional nucleotide may be guanine (G), but is not limited thereto.

More specifically, the gene editing of the present invention may be performed by introducing, into the cells, a guide RNA that specifically binds to a specific sequence of HLA-A, HLA-B or HLA-DR gene or a DNA encoding the guide RNA; and a nucleic acid encoding a Cas protein or the Cas protein itself. That is, one (paternal or maternal) allele of major histocompatibility antigen genes is removed by using the RGEN method employing a CRISPR/Cas system, one of the nucleases, as previously described, which results in only one allele remaining. Finally, the cells having the gene homozygous-like effects can be constructed.

The target sequences that can be used for allele knock-out of HLA-DRB1 gene by the RGEN method may include conserved sequences commonly present in all human beings, for example, 5'-ATCCAGGCAGCATT-GAAGTCAGG-3' (SEQ ID NO: 1), 5'-CCAGGCAGCAT-TGAAGTCAGGTG-3' (SEQ ID NO: 2), 5'-CCTTCCA-GACCCTGGTGATGCTG-3' (SEQ ID NO: 3), or 5'-CCAGACCCTGGTGATGCTGGAAA-3' (SEQ ID NO: 4) that are present in 4HLA-DRB1, but are not limited thereto.

The target sequences that can be used for allele knock-out of HLA-A gene by the RGEN method may include, for example, 5'-CCCTGCGGAGATCACACTGACCT-3' (SEQ ID NO: 5) 5-CCTGCGGAGATCACACTGACCTG-3' (SEQ ID NO: 6), 5'-GAGACCAGGCCTGCA-GGGGATGG-3' (SEQ ID NO: 7), or 5'-CACCTGCCAT-GTGCAGCATGAGG-3' (SEQ ID NO: 8) that are present in HLA-A exon 4, but are not limited thereto.

The target sequences that can be used for allele knock-out of HLA-B gene by the RGEN method may include, for example, 5'-ACCCTGAGGTGCTGGGCCCTGGG-3' (SEQ ID NO: 9), 5'-GATCACACTGACCTGGCAGCGGG-3' (SEQ ID NO: 10), 5'-ACACTGACCTGGCA-GCGGGATGG-3' (SEQ ID NO: 11), 5'-GACCTGGCA-GCGGGATGGCGAGG-3' (SEQ ID NO: 12), or 5'-CCTTCTGGAGAAGAGCAGAGATA-3' (SEQ ID NO: 13) that are present in HLA-B exon 4, but are not limited thereto.

In an embodiment of the present invention, a method of transferring into cells a Cas 9 protein and a sgRNA recognizing a particular HLA gene target sequence to be edited in order to perform allele knock-out of HLA genes was used.

Specifically, the method may be (1) a method in which a Cas 9 protein is overexpressed in bacteria and purified, and a sgRNA (single guided RNA) recognizing a specific HLA target sequence is produced in vitro, followed by transferring them into cells; or (2) a method in which plasmid DNAs expressing the Cas9 protein and sgRNA are transfected into cells and expressed therein, but is not limited thereto.

In addition, in the method for transferring proteins, RNA, or plasmid DNA to the cells according to the present invention, various methods known in the art, such as an electroporation, a liposome, viral vectors, nanoparticles, and a protein translocation domain (PTD) fusion protein method, can be used, but is not limited thereto.

Further, the method of the present invention can be applied to dedifferentiated stem cells (induced pluripotent stem cells), embryonic stem cells as well as to all cells. That is, this is advantageous as a technique that can be applied to various cells.

The method can be applied to all cells, that is, stem cells (induced pluripotent stem cells, embryonic stem cells, somatic cell nuclear transfer derived embryonic stem cells, and adult stem cells) and somatic cells. Also, the cells are derived from human, but not limited thereto.

The adult stem cells mentioned here include all adult stem cells that can be obtained from the human embryo, neonatal and adult bodies, as well as cord blood stem cells, placenta stem cells, Wharton's jelly stem cells, amniotic fluid stem cells, amniotic epithelial cells, extraembryonic stem cells and genetically modified cells that are derived therefrom.

Further, the somatic cells mentioned here include all cells that can be obtained from the embryo as well as neonatal and adult bodies, and also all genetically modified cells that are derived therefrom.

When two or more genes of HLA-A, HLA-B and HLA-DR have heterozygous genotypes, or when HLA-A, and HLA-B genes have heterozygous genotypes, the method of producing immune-compatible cells according to the present invention can sequentially or simultaneously delete or modify alleles of heterozygous genes from the corresponding cells by gene editing, and particularly can be performed sequentially, but is not limited thereto.

Further, when HLA-A, HLA-B and HLA-DR genes all have heterozygous genotypes or when HLA-A, and HLA-B genes have heterozygous genotypes, the production method can delete or modify one or two allele of the respective genes from the separated cells by gene editing, and the alleles of the respective genes can be sequentially or simultaneously deleted or modified by the gene editing. In addition, the production method may comprise the steps of removing one pair of alleles of HLA-DR genes in a separated cell in which HLA-A, HLA-B and HLA-DR genes all have heterozygous genotypes by gene editing, and removing or modifying one or two allele of each of HLA-A and HLA-B genes by gene editing, but is not limited thereto. Since DRB1 is expressed only in some cells such as B cells as one of the MHC class II proteins, there are advantages in that biallelic knock-out is possible and the types of HLA combinations can be simplified, but they are not limited thereto. According to this method, it is possible to produce four different homozygous-like cells in one type of cell.

Figure 14:
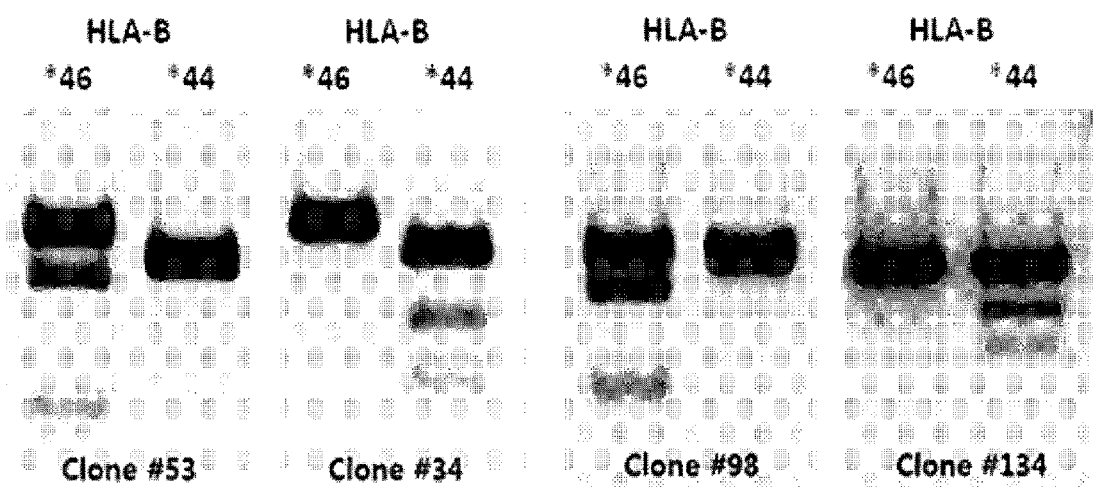
FIG. 14 shows the results of analyzing HLA-B genotypes of #53, #34, #98, and #134 clones.
Figure 16:
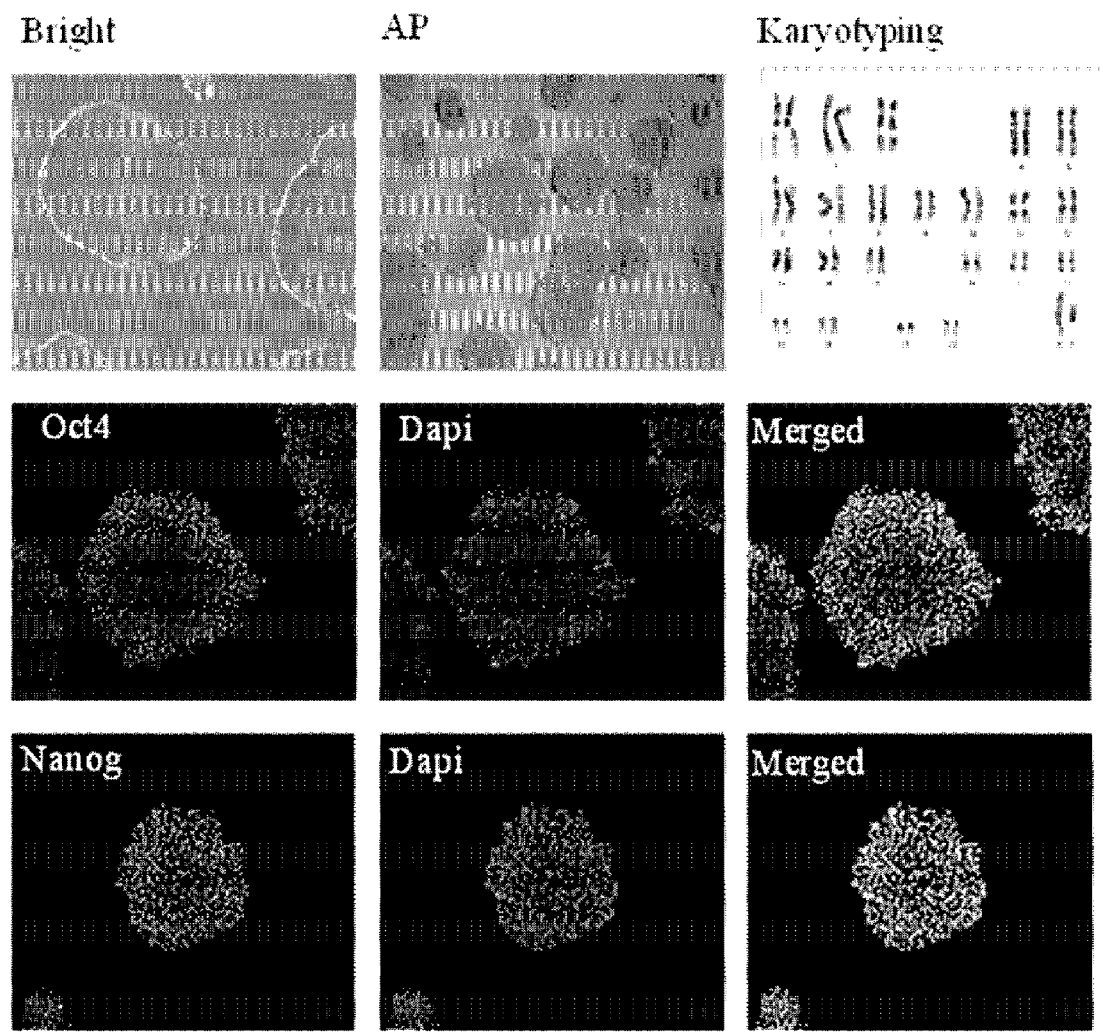
FIG. 16 shows the results of identifying the pluripotency of H9 clone having HLA-A*02$^+$/*03$^-$ and HLA-B*35$^+$/*44$^-$ genotype and in which both alleles of DRB1 genes are knocked out.

In a specific embodiment of the present invention, the embryonic stem cell and the induced pluripotent stem cell were subjected to biallelic knock-out to disrupt a Drb1 gene (FIG. 9), and then, one allele of each of HLA-A and HLA-B genes was removed by gene editing to thereby produce four different homozygous-like cells (FIGS. 14 and 15).

Moreover, the production method of the present invention may further comprise the step of removing or modifying alleles of one or more genes selected from HLA-C, HLA-DP and HLA-DQ in addition to HLA-A, HLA-B and HLA-DR genes, by gene editing. It is obvious that for this gene editing, those previously described are applied.

In addition, the production method of the present invention may further comprising analyzing the HLA type of the cells produced. This step can be performed by using various methods known in the art for analyzing the genotype. For example, this step can be performed through the method of amplifying a target sequence region of the HLA gene of interest by PCR and then analyzing the sequence thereof, but is not limited thereto.

Further, the above method may further comprising selecting cells having HLA type to be transplanted from the produced immune-compatible cell group. In such a selection step, this may precede a step of analyzing an HLA genotype. When the HLA genotype is analyzed, the desired cells can be selected by the analysis result. This process may provide an appropriate HLA type of cells to recipients.

In another embodiment of the present invention, the immune-compatible cells produced by the production method are provided.

Details of this production method are as described above.

In another embodiment, the present invention provides cell populations comprising the immune-compatible cells produced by the production method.

Details of this production method are as described above. The above cell populations may also be referred to as a cell bank.

In another embodiment, the present invention provides a method for producing an immune-compatible cell population comprising (a) editing one or two allele of immune-compatible antigen genes by gene deletion or modification in an isolated cell, wherein at least one of the immune-compatible antigen genes selected from HLA-A, HLA-B and HLA-DRB1 has a heterozygous genotype, or in an isolated cell, wherein at least one of the immune-compatible antigen genes selected from HLA-A and HLA-B has a heterozygous genotype; and (b) collecting the cells produced in the step (a).

Details of the step (a) are as previously described. Also, the cell population may be referred to as a cell bank.

In the step (b), a population of cells having various HLA genotypes can be constructed by collecting the cells produced in the step (a).

In addition, after performing the step (a) and before performing the step (b), the production method of the present invention may further comprise: (a') identifying HLA genotypes of the isolated cells obtained from the step (a), thus producing the HLA genotype-identified cell population, that is, a cell population.

Mode for Invention

Below, the present invention will be described in detail by way of examples. However, the examples are intended only to illustrate the invention, and to not limit the present invention.

It is known that the most important HLA molecules to match for are class I HLA-A, HLA-B and class II HLA-DR. To create an HLA-A homozygous human pluripotent stem cell library, we designed gRNAs to target Cas9 to the Drb1, HLA-A and HLA-B genes and tested the ability to direct site-specific mutations in both ES cells and iPS cells. FIG. 1 is a schematic diagram summarizing our strategy.

Materials and Methods

Cell Culture hESCs and iPSCs were maintained on Geltrex (Invitrogen) coated plates in E8 medium (Invitrogen) supplemented with 10 µM ROCK inhibitor Y27632 (Santa Cruz) for 24 h. Cells were passaged with EDTA every 4 days to 5 days.

Guide RNA

RNA was transcribed in vitro by using the MEGAshortscript T7 kit (Ambion) according to the manufacturer's manual. Templates for sgRNA were generated by annealing and extension of two complementary oligonucleotides. The guide RNA sequences have the same sequence of target DNA and are 23 nt sequence wherein the 3' end of the sequence is "NGG".

Transfection hESCs and iPSCs were transfected with the Amaxa P3 Primary Cell 4DNucleofector Kit using Program CB-150 according to the manufacturer's protocol. Briefly, 2×10⁵ cells were transfected with Cas9 protein from Toolgen (30 µg) premixed with in vitro transcribed sgRNA (40 µg). Cas9 protein was mixed with sgRNA dissolved in nuclease-free water and incubated for 10 min at room temperature. No more than 10 µL of the Cas0-sgRNA mixture was added to 100 µL of the Nucleofection solution. Cells were analyzed 3 days after transfection.

T7E1 Assay

Genomic DNA was extracted using the DNeasy Blood & Tissue Kit (QIAGEN). PCR amplicons including Cas9 target sites were generated using PicoMaxx High Fidelity PCR system (Agilent). The PCR amplicons were denatured by heating and annealed to form heteroduplex DNA using a thermocycler and then digested with T7 endonuclease 1 (New England Biolabs) for 20 min at 37° C., and then analyzed using agarose gel electrophoresis. For sequencing analysis, the PCR products were used for sub-cloning using the TA cloning vector (pGEM-T Easy Vector; Promega). The reconstructed plasmids were purified, and the individual clones were sequenced (Macrogen Inc.).

Alkaline Phosphatase Staining

Alkaline phosphatase staining was performed using the Alkaline Phosphatasees Staining Kit II (Stemgent) according to the manufacturer's instructions. The cells were fixed in 4% paraformaldehyde, washed with Tris-buffered saline/0.05% Tween 20 (Sigma), and stained with AP staining solution.

Immunofluorescence hESCs were fixed with 4% formaldehyde and permeabilized with 0.1% Triton X-100 in phosphate-buffered saline (PBS; Invitrogen) for 30 min at room temperature. The cells were then washed with 0.03% Triton X-100 in PBS (washing buffer). The fixed samples were blocked for 1 h with 5% bovine serum albumin solution dissolved in wash buffer followed by incubation for 24 h at 4° C. with primary antibodies. The samples were washed with washing buffer and then incubated with FITC conjugated secondary antibodies (Molecular Probes) for 2 h. The slides were counterstained with DAPI (Vector Laboratories) to stain the cell nuclei.

Targeted Deep Sequencing.

Genomic DNA segments spanning the on-target and potential off-target sites were amplified using Phusion polymerase (New England BioLabs). The resulting PCR amplicons were subjected to paired-end sequencing using Illumina MiSeq.

Karyotyping

Karyotyping was analyzed by GenDix Inc.

Example 1: Production of Homozygous-Like Cells Through Monoallelic Knock-Out of HLA-A, HLA-B and HLA-DRB1 Genes Through the genome editing in an isolated cell in which human leukocyte antigen (HLA)-A, HLA-B and HLA-DR genes have heterozygous genotypes, monoallelic knock-out of HLA-A, HLA-B and HLA-DRB1 genes was performed by using a nuclease to thereby construct eight types of cells in which the HLA-A, HLA-B and HLA-DRB1 genes have homozygous-like properties. The above process was shown in the schematic diagram in FIG. 2.

Example 2: Production of Homozygous-Like Cells Through Monoallelic Knock-Out of HLA-A and HLA-B Genes and Biallelic Knock-Out of HLA-DRB1 Gene Through the genome editing in an isolated cell in which HLA-A, HLA-B and HLA-DRB1 genes have heterozygous genotypes, one pair of alleles of the HLA-DRB1 gene was removed, and monoallelic knock-out of the HLA-A and HLA-B genes was performed by using a nuclease to thereby construct four kinds of cells in which the HLA-A and HLA-B genes have homozygous-like properties. The above process was shown in the schematic diagram in FIG. 3.

Example 3: Introduction of Plasmid Expressing Cas9 Protein and HLA-DRB1-Specific Guide RNA (DRB1 gRNA) into Human Induced Pluripotent Stem Cells Plasmid DNAs expressing a Cas9 protein and a DRB1 gRNA were delivered into a human induced pluripotent stem cell #12 (iPSC#12) by electroporation. Then, the genomic DNA of the resulting colonies derived from the iPSC#12 was extracted. Thereafter, whether the indel (insertion or deletion) was induced at the target sequence within the DRB1 gene was analyzed by a T7 endonuclease I (T7E1) mutation detection assay, and the results are shown in FIG. 4.

Figure 4:
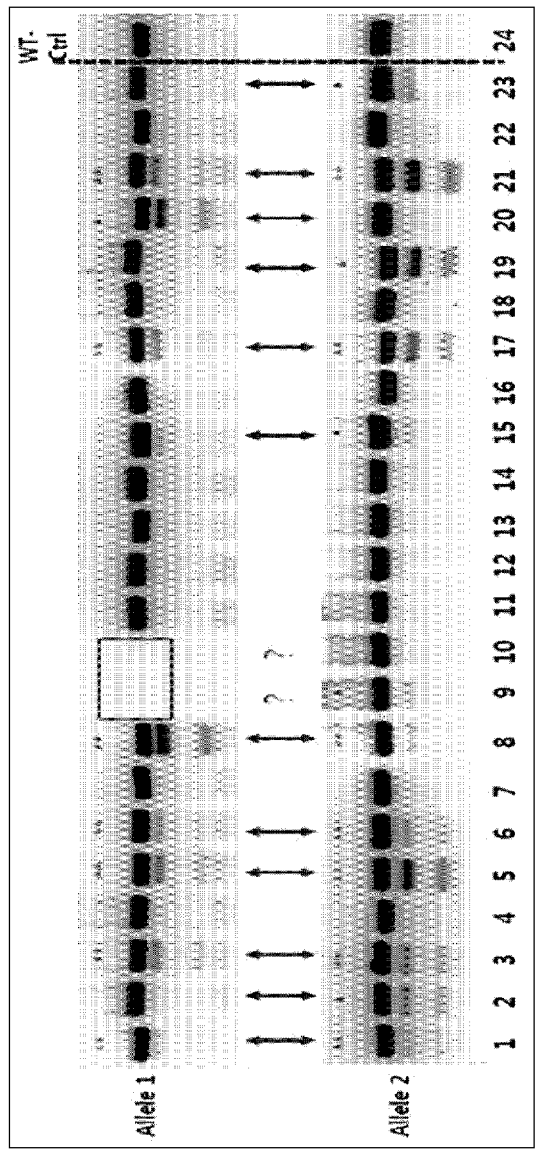
FIG. 4 shows the results of analyzing whether or not, after plasmids expressing Cas9 proteins and DRB1 guide RNA are introduced into a human induced pluripotent stem cell #12 via electroporation, the indel is induced in the site of the target sequences in the DRB1 gene.

As shown in FIG. 4, as a result of the analysis, among 23 iPSC cell lines, iPSCs in which the indel has been induced at both (paternal and maternal) alleles of the DRB1 gene were determined as 7 cell lines (red arrow); iPSC in which the indel has been induced at the allele #1 (shown as allele 1) was determined as 1 cell line (purple arrow); and iPSCs in which the indel has been induced at the allele #2 (shown as allele 2) was determined as 4 cell lines (blue arrow).

Example 4: Introduction of Cas 9 Protein and HLA-DRB1-Specific Guide RNA (DRB1 gRNA) into Human Induced Pluripotent Stem Cells Using Electroporation A Cas9 protein and an HLA-DRB1 gRNA, not a plasmid DNA, were delivered into human induced pluripotent stem cell #8 (iPSC #8) by electroporation. Then, the genomic DNA of the resulting colonies derived from the iPSC#8 was extracted. Thereafter, whether the indel (insertion or deletion) was induced at the target sequence within the HLA-DRB1 gene was analyzed by a T7 endonuclease I (T7E1) mutation detection assay, and the results are shown in FIG. 5.

Figure 5:
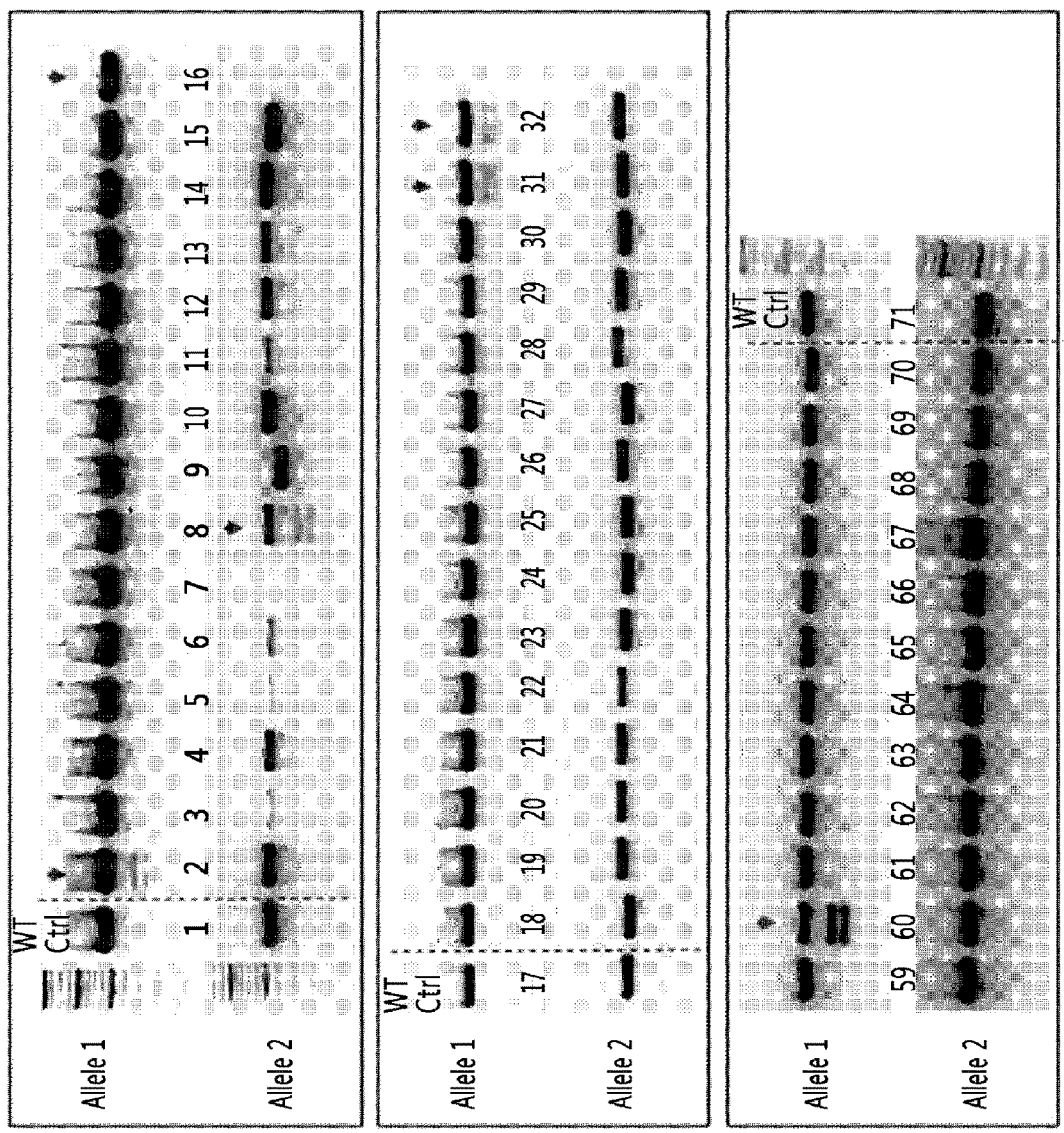
FIG. 5 shows the results of analyzing whether or not, after Cas9 proteins and DRB1 guide RNA are introduced into a human induced pluripotent stem cell #8 via electroporation, the indel is induced in the site of the target sequences in the DRB1 gene.

As shown in FIG. 5, as a result of the analysis, among total 75 iPSC cell lines, iPSCs in which the indel had been induced at the allele #1 of the DRB1 gene (shown as allele 1) were determined as seven cell lines (red arrow); and iPSCs in which the indel has been induced at the allele #2 (shown as allele 2) were determined as two cell lines (blue arrow). FIG. 5 shows the results of the agarose gel analysis of 42 cell lines out of the total of 75 iPSC cell lines analyzed.

Also, it has been found in FIG. 5 that as a result of inducing the indel using the human induced pluripotent stem cell #8 (iPSC #8), clone #8 has been identified to include the indel at the allele 2 (see FIG. 5). In order to verify this, the target sequence region was amplified by PCR, followed by sequence analysis. The results are shown in FIG. 6.

Figure 6:
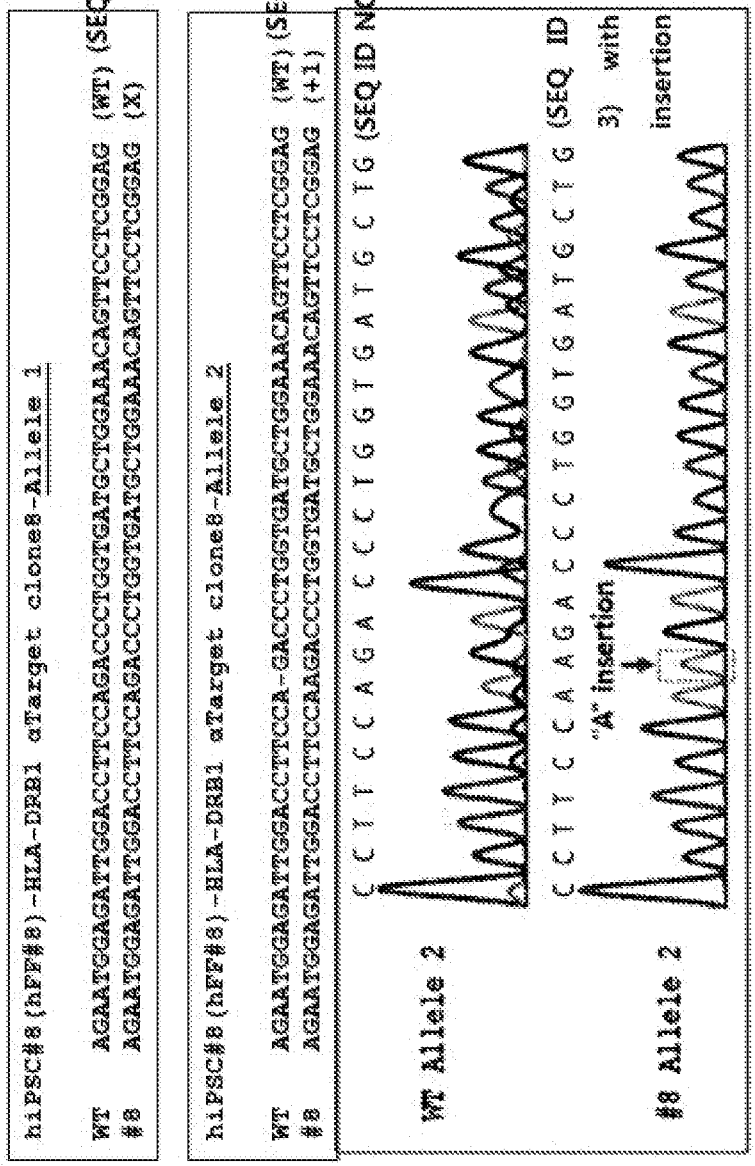
FIG. 6 shows the results of identifying whether the indel is present in Allele 2 of clone #8 among the clones identified in FIG. 5 through a sequence analysis.

As a result, as shown in FIG. 6, it was confirmed that there was no change in the allele 1, but one nucleotide ("A") was inserted in the allele 2.

Further, the Cas9 protein and HLA-DRB1 gRNA, not plasmid DNA, were delivered into human induced pluripotent stem cell #12 (iPSC #12) by electroporation. Then, the genomic DNA of the resulting colonies derived from the iPSC #12 was extracted. Thereafter, whether the indel (insertion or deletion) was induced at the target sequence within the HLA-DRB1 gene was analyzed by a T7 endonuclease I (T7E1) mutation detection assay, and the results are shown in FIG. 7.

Figure 7:
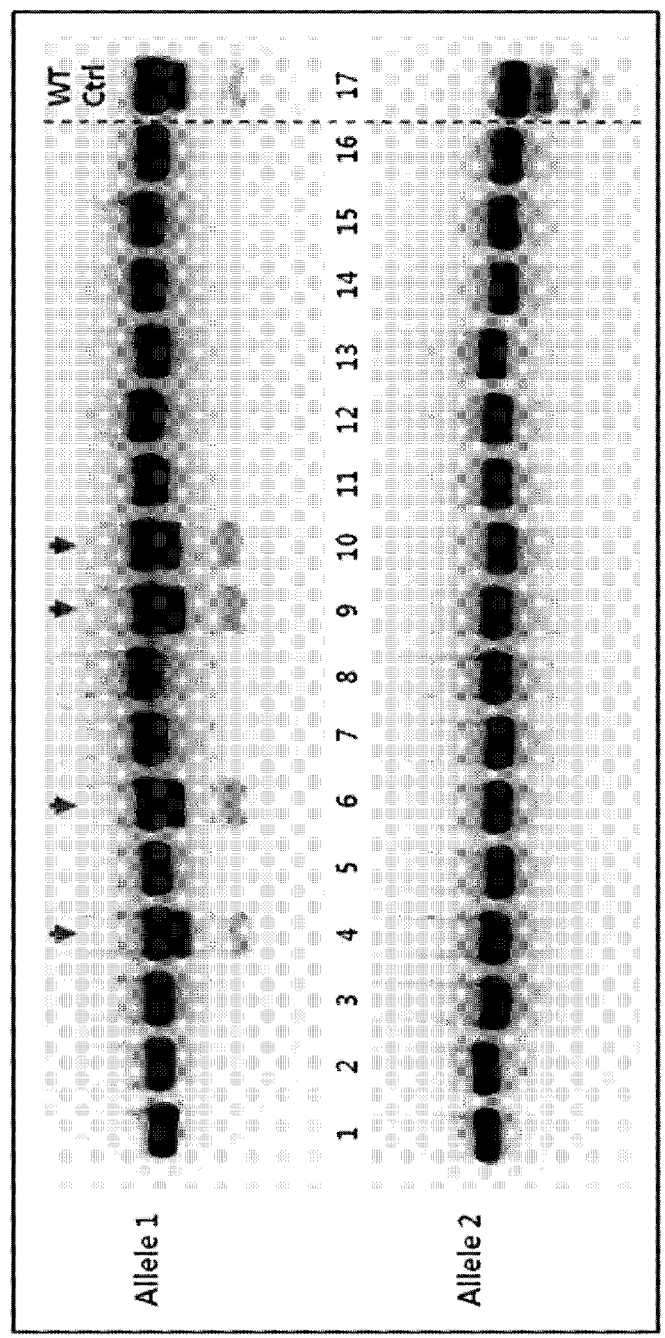
FIG. 7 shows the results of analyzing whether or not, after Cas9 proteins and DRB1 guide RNA are introduced into a human induced pluripotent stem cell #12 via electroporation, the indel is induced in the site of the target sequences in the DRB1 gene.

As shown in FIG. 7, the analysis results showed that in the clones #4, #6, #9, and #10, the indel was present in the allele 1, and there was no change in the allele 2.

In FIG. 7, among the clones #4, #6, #9, and #10, in which it was shown to have the indel at the allele 1, the clone #4 was selected and subject to verification for the presence of the indel. For this, the target sequence regions of the alleles 1 and 2 were amplified by PCR and then subjected to sequence analysis. The results are shown in FIG. 8.

Figure 8:
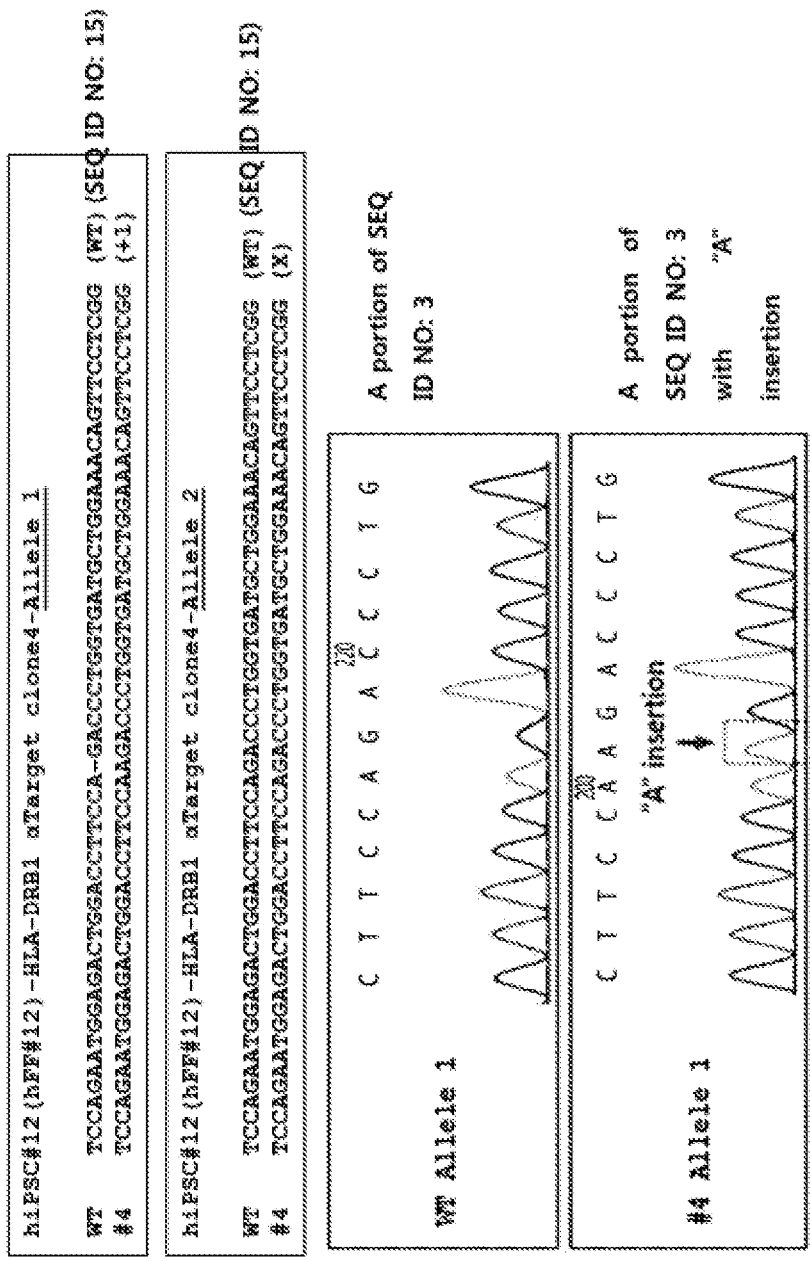
FIG. 8 shows the results of identifying whether the indel is present in Allele 1 of clone #4 among the clones identified in FIG. 7 through a sequence analysis.

As a result, as shown in FIG. 8, it was confirmed that one nucleotide ("A") was inserted at the allele 1 and there was no change in the allele 2.

Example 5: Establishment of Completely Knocked Out Drb1 Pluripotent Stem Cell Lines Class II proteins are expressed primarily on B lymphocytes, macrophages, and dendritic cells. Unlike class I, their loss does not trigger NK cell mediated cell lysis. Therefore we created completely knocked out Drb1 hESCs.

To do this, purified recombinant Cas9 protein was complexed with in vitro transcribed sgRNA targeting Drb1 locus. The resulting protein-RNA complex was transfected into the H9, CHA15 hES and hiPSC12 lines via electroporation. At 72 h post transfection, cells were dissociated and replaced as single cells at a very low density in hESC medium supplemented with Rho kinase (ROCK) inhibitor.

To validate the Drb1 knock-out, we performed deep sequencing and Sanger sequencing. Among selected representative clones H9, #85 showed 5 nt and 13 nt deletion patterns, CHA15 #34 showed 1 nt insertion of both alleles, and 1 nt insertion and 32 nt deletion patterns were observed in hiPSC12 clone #13 (FIG. 9). All of our Drb1 knock-out clones exhibited stable growth and displayed round, tightly packed morphology over 10 passages.

Figure 10:
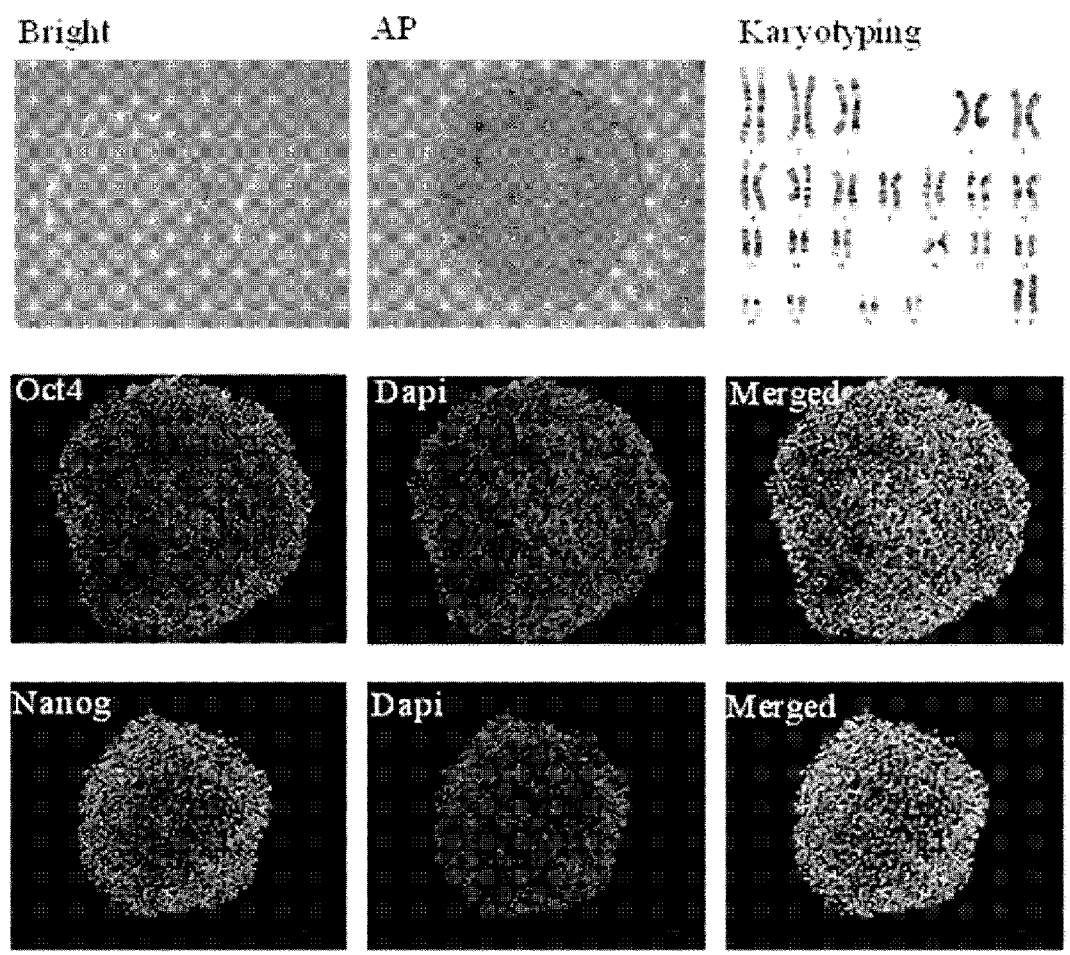
FIG. 10 shows the results of identifying the pluripotency of the clones identified in FIG. 9.

To further validate the pluripotency of our clones, we performed immunostaining. Immunocytochemical analysis confirmed that the Drb1 KO clones properly express the pluripotency marker Oct4, Nanog, AP and no karyotype abnormalities were observed (FIG. 10).

Example 6: Establishment of Drb1 Knock-Out, and HLA-A and HLA-B Homozygote Pluripotent Stem Cell Lines To have 4 HLA-A and B homozygote cell lines, we next targeted HLA-A and HLA-B in Dr1b KO clones.

Figure 11:
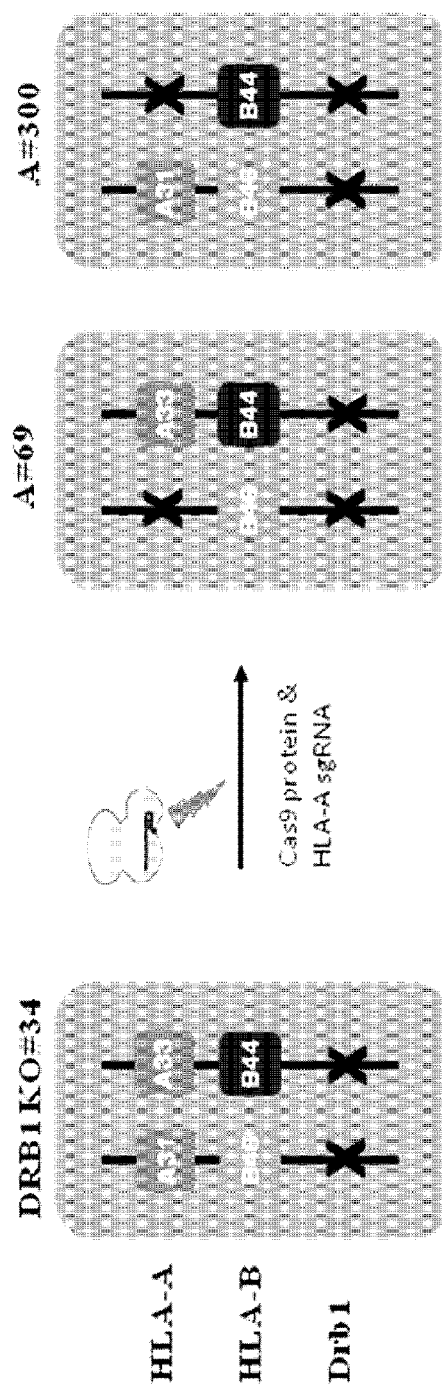
FIG. 11 is a schematic diagram showing a process of knocking out one allele of HLA-A gene in cells that have both alleles of the DRB1 gene knocked out, by using Cas9 protein and HLA-A sgRNA.

By using Cas9 protein and an in vitro transcribed sgRNA delivery method again, we first established HLA-A monoallelic mutant cells. Sequencing of single cell derived clones was analyzed to identify the clones which have monoallelic indel patterns on targeted regions. FIG. 11 summarizes skim and mutation patterns of HLA-A monoallelic mutant clones derived from the Drb1 KO CHA 15 hES cell line.

Figure 12:
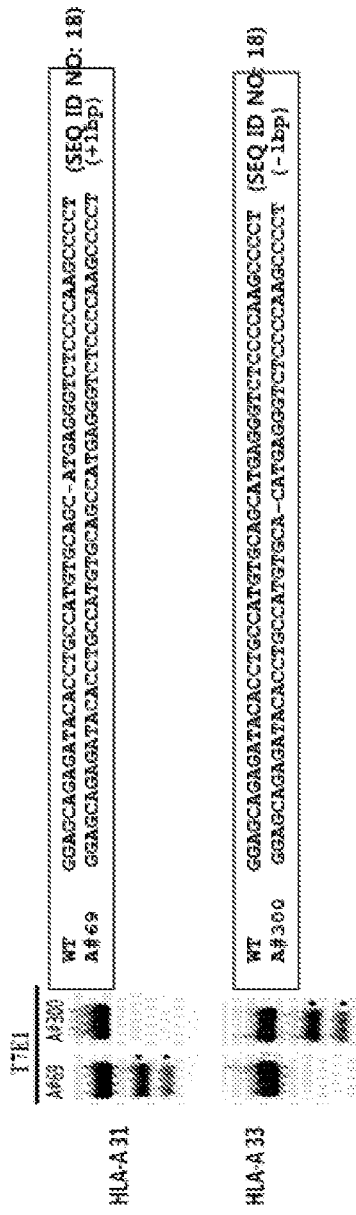
FIG. 12 shows the results of analyzing HLA-A genotypes and sequences of A#69 and A#300 clones.

T7E1 analysis of allele specific amplified PCR products showed specific cleavage on one allele only. Sequencing results further validated that clone A#69 has 1 nt insertion on allele A*31 and clone A#300 has 1 nt deletion on allele A*33 (FIG. 12).

Figure 13:
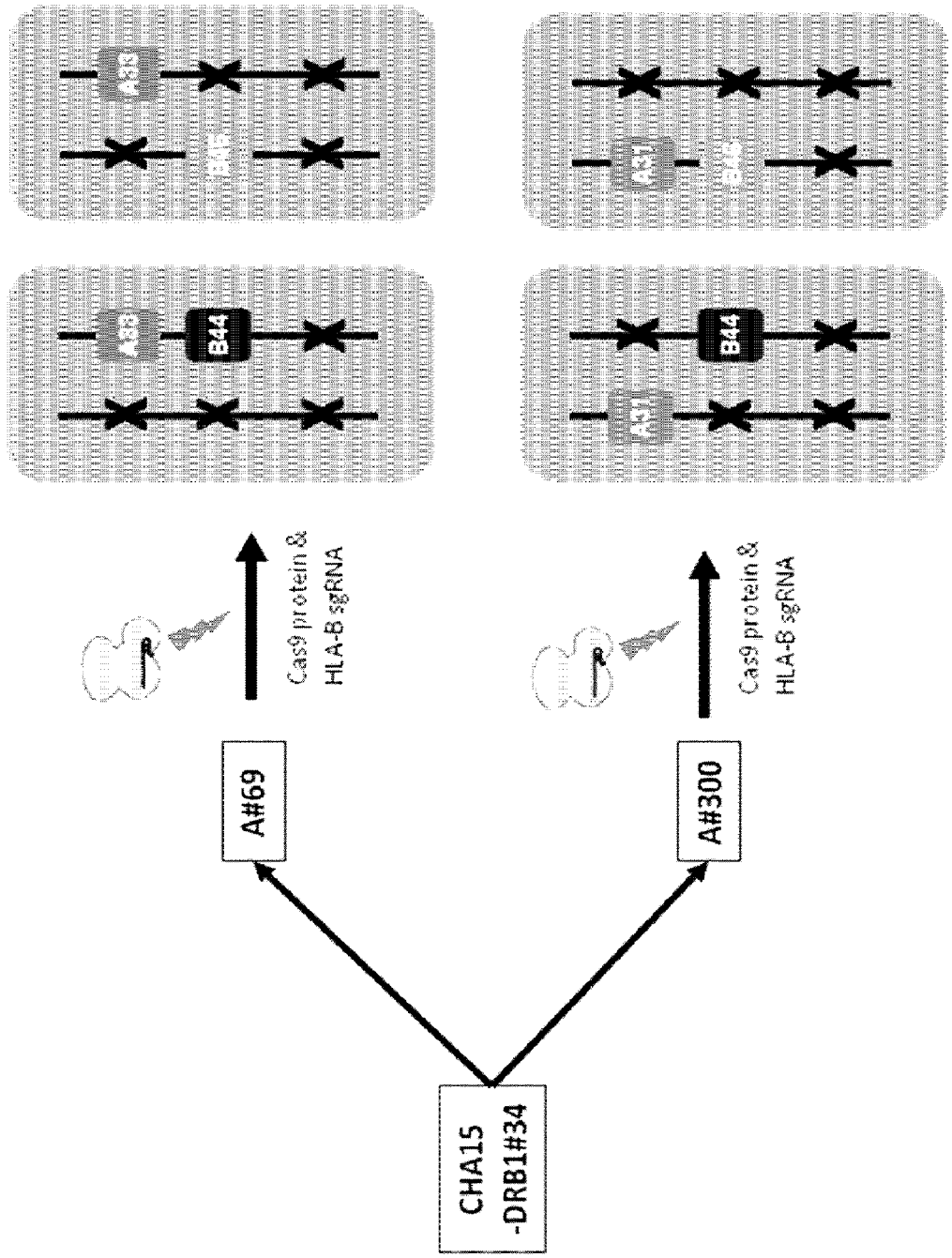
FIG. 13 is a schematic diagram showing a process of knocking out one allele of HLA-B gene using Cas9 proteins and HLA-B sgRNA in the clones identified in FIG. 12.

After validation of HLA-A mutation, we introduced sgRNA targeting HLA-B gene (FIG. 13). Clones were examined by allele specific T7E1 and sequencing. FIGS. 14 and 15 show representative clones derived from CHA15 hES cell lines. Parallel experiments were also performed in H9 hES and iPS12.

The present inventors did not observe any morphological or growth abnormalities in our clones. Finally, we further characterized the pluripotency of one H9 clone which has Drb1 complete KO, HLA-A*02$^+$/*03$^-$ and HLA-B *35$^+$/*44$^-$ genotypes Immunocytochemical analysis confirmed that these cells expressed the pluripotency marker Oct4 and Nanog.

The present inventors' study demonstrates that HLA homozygote human pluripotent stem cell can be generated easily by using CRISPR-Cas9 mediated genetic intervention. Here we generated a small library of these clones form pre-existing pluripotent cell lines. This is significant because our protocol eliminates SNT or factor mediated reprogramming, which typically requires time-consuming and costly cell isolation procedures to have donor-recipient matched cell lines. The inventors anticipate that our protocol will accelerate the translation of cell based therapies from bench to bedside by providing patient immune-matched pluripotent stem cells. Importantly, using well characterized cell lines derived under GMP conditions will substantially reduce initial costs. Moreover, protein based delivery of Cas9, rather than delivery in plasmid form, prevents potential integration of plasmid vectors into a genome.

In summary, the inventors' study allows generation of patient immune-matched pluripotent stem cells from easily available hES or iPSC lines.

From the foregoing description, those skilled in the art to which this invention pertains can understand that the present invention may be embodied in other specific forms without changing the technical spirit or essential characteristics of the invention. In this connection, the above described examples should be understood as exemplary and as not limiting in all aspects. It must be interpreted that all changes or modified forms derived from the meaning and range of the appended claims and the equivalents thereof, rather than the foregoing detailed description, are included in the scope of the present invention.

The invention claimed is:

1. A method for producing immune-compatible cells, comprising deleting or modifying only one allele of each of HLA-A and HLA-B genes by gene editing in an isolated cell in which one or both of the HLA-A and HLA-B genes are heterozygous, and further performing knock-out of one pair of alleles of HLA-DR gene.

2. The method for producing immune-compatible cells of claim 1, wherein the gene deletion is performed by gene knock-out, or the gene modification is performed via gene knock-in.

3. The method for producing immune-compatible cells of claim 1, wherein the gene editing is performed by using an HLA-A specific engineered nuclease, an HLA-B specific engineered nuclease, or an HLA-DR specific engineered nuclease.

4. The method for producing immune-compatible cells of claim 3, wherein the engineered nuclease is selected from the group consisting of zinc finger nuclease (ZFN), transcription activator-like effector nuclease (TALEN), and RNA-guided engineered nuclease (RGEN) that includes a Cas protein and a guide RNA that specifically binds to a particular sequence of the HLA-A, HLA-B, or HLA-DR genes.

5. The method for producing immune-compatible cells of claim 4, wherein the gene editing is performed by introducing into cells a guide RNA specifically binding to a particular sequence of the HLA-A, HLA-B, or HLA-DR genes or DNA encoding the guide RNA; and a nucleic acid encoding a Cas protein or the Cas protein itself.

6. The method for producing immune-compatible cells of claim 5, wherein the guide RNA is a dualRNA comprising crRNA and tracrRNA or a single-strand guide RNA.

7. The method for producing immune-compatible cells of claim 6, wherein the Cas protein is a Cas9 protein.

8. The method for producing immune-compatible cells of claim 1, wherein the cells are stem cells or somatic cells.

9. The method for producing immune-compatible cells of claim 8, wherein the stem cells are induced pluripotent stem cells, embryonic stem cells, somatic cell nuclear transfer derived embryonic stem cells, or adult stem cells.

10. The method for producing immune-compatible cells of claim 1, further comprising removing alleles of one or more genes selected from HLA-C, HLA-DP, and HLA-DQ by gene editing.

11. The method for producing immune-compatible cells of claim 1, further comprising analyzing the HLA type of the cells produced.

12. An isolated cell population comprising the immune-compatible cells produced by the method of claim 1.

13. A method for producing an immune-compatible cell population comprising (a) deleting or modifying only one allele of each of HLA-A and HLA-B genes by gene editing in an isolated cell in which one or both of the HLA-A and HLA-B genes are heterozygous, and further performing knock-out of one pair of alleles of HLA-DR gene; and (b) collecting the cells produced in step (a).

14. The method for producing an immune-compatible cell population of claim 13, further comprising (a') identifying HLA genotypes of the isolated cell obtained from step (a) after performing the step (a) and before performing step (b).

* * * * *